(12) United States Patent
Bolduc et al.

(10) Patent No.: US 7,491,232 B2
(45) Date of Patent: Feb. 17, 2009

(54) CATHETER-BASED FASTENER IMPLANTATION APPARATUS AND METHODS WITH IMPLANTATION FORCE RESOLUTION

(75) Inventors: Lee Bolduc, Sunnyvale, CA (US); Juan C. Parodi, St. Louis, MO (US)

(73) Assignee: Aptus Endosystems, Inc., Sunnyvale, CA (US)

( * ) Notice: Subject to any disclaimer, the term of this patent is extended or adjusted under 35 U.S.C. 154(b) by 655 days.

(21) Appl. No.: 10/669,881

(22) Filed: Sep. 24, 2003

(65) Prior Publication Data

US 2004/0127916 A1  Jul. 1, 2004
US 2005/0256531 A9  Nov. 17, 2005

Related U.S. Application Data

(60) Continuation-in-part of application No. 10/307,226, filed on Nov. 29, 2002, and a continuation-in-part of application No. 10/271,334, filed on Oct. 15, 2002, now Pat. No. 6,960,217, and a continuation-in-part of application No. 10/099,149, filed on Mar. 15, 2002, now Pat. No. 6,800,081, which is a division of application No. 09/787,135, filed on Jun. 4, 2001, now Pat. No. 6,592,593.

(60) Provisional application No. 60/333,937, filed on Nov. 28, 2001, provisional application No. 60/101,050, filed on Sep. 18, 1998.

(51) Int. Cl.
*A61F 2/06* (2006.01)
(52) U.S. Cl. .................... 623/1.36; 623/1.11
(58) Field of Classification Search ............. 623/1.36, 623/1.11
See application file for complete search history.

(56) References Cited

U.S. PATENT DOCUMENTS

| 2,033,039 | A | 3/1936 | Limpert |
| 3,499,222 | A | 3/1970 | Linkow et al. |
| 3,686,740 | A | 8/1972 | Shiley |

(Continued)

FOREIGN PATENT DOCUMENTS

EP          0 321 912          12/1987

(Continued)

OTHER PUBLICATIONS

5mm Origin Tracker™ It Runs In Circles Around Staples, 1995 Advertising Literature.

(Continued)

*Primary Examiner*—(Jackie) Tan-Uyen T. Ho
*Assistant Examiner*—Melissa Ryckman
(74) *Attorney, Agent, or Firm*—Ryan Kromholz & Manion S.C.

(57) ABSTRACT

Apparatus and methods implant a fastener in a targeted body region, e.g., a hollow body cavity or an intraluminal space. The apparatus and methods deploy in the targeted body region a fastener attachment assembly that carries an actuated member. The actuated member is selectively operable to generate an implantation force to implant a fastener into tissue within the targeted body region. The fastener can be implanted, e.g., to secure a prosthesis, e.g., an endovascular graft. The systems and apparatus apply a resolution force at or near the actuated member, thereby making possible a stable and dependable catheter-based fastening platform.

16 Claims, 38 Drawing Sheets

U.S. PATENT DOCUMENTS

| | | | |
|---|---|---|---|
| 3,799,172 A | 3/1974 | Szpur | |
| 4,140,126 A | 2/1979 | Choudhury | |
| 4,307,722 A | 12/1981 | Evans | |
| 4,580,568 A | 4/1986 | Gianturco | |
| 4,625,597 A | 12/1986 | Cast | |
| 4,781,682 A | 11/1988 | Patel | |
| 4,898,577 A | 2/1990 | Badger et al. | |
| 4,921,484 A | 5/1990 | Hillstead | |
| 5,030,204 A | 7/1991 | Badger et al. | |
| 5,042,707 A * | 8/1991 | Taheri | 606/213 |
| 5,071,407 A | 12/1991 | Termin et al. | |
| 5,104,399 A | 4/1992 | Lazarus | |
| 5,207,695 A | 5/1993 | Trout, III | |
| 5,290,295 A | 3/1994 | Querals et al. | |
| 5,330,490 A | 7/1994 | Wilk et al. | |
| 5,330,503 A | 7/1994 | Yoon | |
| 5,456,714 A | 10/1995 | Owen | |
| 5,470,337 A | 11/1995 | Moss | |
| 5,480,382 A | 1/1996 | Hammerslag et al. | |
| 5,489,295 A | 2/1996 | Piplani et al. | |
| 5,562,728 A | 10/1996 | Lazarus et al. | |
| 5,571,171 A | 11/1996 | Barone et al. | |
| 5,571,173 A | 11/1996 | Parodi | |
| 5,582,616 A | 12/1996 | Bolduc et al. | |
| 5,626,613 A | 5/1997 | Schmieding | |
| 5,639,278 A | 6/1997 | Dereume et al. | |
| 5,662,683 A | 9/1997 | Kay | |
| 5,662,700 A | 9/1997 | Lazarus | |
| 5,676,696 A | 10/1997 | Marcade | |
| 5,676,697 A | 10/1997 | McDonald | |
| 5,700,269 A | 12/1997 | Pinchuk et al. | |
| 5,702,365 A | 12/1997 | King | |
| 5,713,907 A | 2/1998 | Hogendijk et al. | |
| 5,762,458 A | 6/1998 | Wang et al. | |
| 5,810,882 A | 9/1998 | Bolduc et al. | |
| 5,814,016 A | 9/1998 | Valley et al. | |
| 5,824,008 A | 10/1998 | Bolduc et al. | |
| 5,824,041 A | 10/1998 | Lenker et al. | |
| 5,855,565 A | 1/1999 | Bar-Cohen et al. | |
| 5,944,750 A * | 8/1999 | Tanner et al. | 623/1.23 |
| 5,957,940 A | 9/1999 | Tanner et al. | |
| 5,964,772 A | 10/1999 | Bolduc et al. | |
| 5,968,053 A | 10/1999 | Revelas | |
| 5,972,023 A | 10/1999 | Tanner et al. | |
| 5,980,548 A | 11/1999 | Evans et al. | |
| 5,993,401 A | 11/1999 | Inbe et al. | |
| 5,993,466 A | 11/1999 | Yoon | |
| 6,070,589 A | 6/2000 | Keith et al. | |
| 6,077,297 A | 6/2000 | Robinson et al. | |
| 6,086,582 A | 7/2000 | Altman et al. | |
| 6,126,685 A | 10/2000 | Lenker et al. | |
| 6,145,509 A | 11/2000 | Tanner | |
| 6,146,339 A | 11/2000 | Biagtan et al. | |
| 6,217,597 B1 | 4/2001 | Tanner | |
| 6,248,118 B1 | 6/2001 | Tanner et al. | |
| 6,258,119 B1 | 7/2001 | Hussein et al. | |
| 6,270,516 B1 | 8/2001 | Tanner et al. | |
| 6,287,315 B1 | 9/2001 | Wijeratne et al. | |
| 6,296,656 B1 | 10/2001 | Bolduc et al. | |
| 6,302,906 B1 | 10/2001 | Goicoechea et al. | |
| 6,309,403 B1 | 10/2001 | Minor et al. | |
| 6,336,933 B1 | 1/2002 | Parodi | |
| 6,371,919 B1 | 4/2002 | Tanner et al. | |
| 6,409,757 B1 | 6/2002 | Trout, III et al. | |
| 6,428,565 B1 | 8/2002 | Wisselink | |
| 6,458,152 B1 | 10/2002 | Khosravi et al. | |
| 6,482,224 B1 | 11/2002 | Michler et al. | |
| 6,520,974 B2 | 2/2003 | Tanner et al. | |
| 6,544,253 B1 | 4/2003 | Tanner | |
| 6,562,051 B1 | 5/2003 | Bolduc et al. | |
| 6,592,593 B1 | 7/2003 | Parodi et al. | |
| 6,652,572 B2 | 11/2003 | Kugler et al. | |
| 6,719,174 B1 | 4/2004 | Swift | |
| 6,730,119 B1 | 5/2004 | Smalling | |
| 6,800,081 B2 | 10/2004 | Parodi | |
| 6,960,217 B2 | 11/2005 | Bolduc | |

FOREIGN PATENT DOCUMENTS

| | | |
|---|---|---|
| EP | 0 663 184 | 1/1994 |
| FR | 2299548 | 1/1975 |
| WO | WO 97/03616 | 2/1997 |
| WO | WO 99/53845 | 10/1999 |
| WO | WO 00/16701 | 3/2000 |

OTHER PUBLICATIONS

"The Spiral Tracker: A New Technique for Stabilizing Prosthetic Mesh in Laparoscopic Hernia Repair", Nov. 1995 *Surgical Rounds*.

"Laparoscopic Surgery", *MedPro Month Oct. 1995*, p. 190.

"Assisted TAPP Procedure", Newman III et al., Circa 1995

"Extraperitoneal Endoscopic Burch Repair Using a Tacker Mesh Technique", Hatchett et al., Circa 199.

* cited by examiner

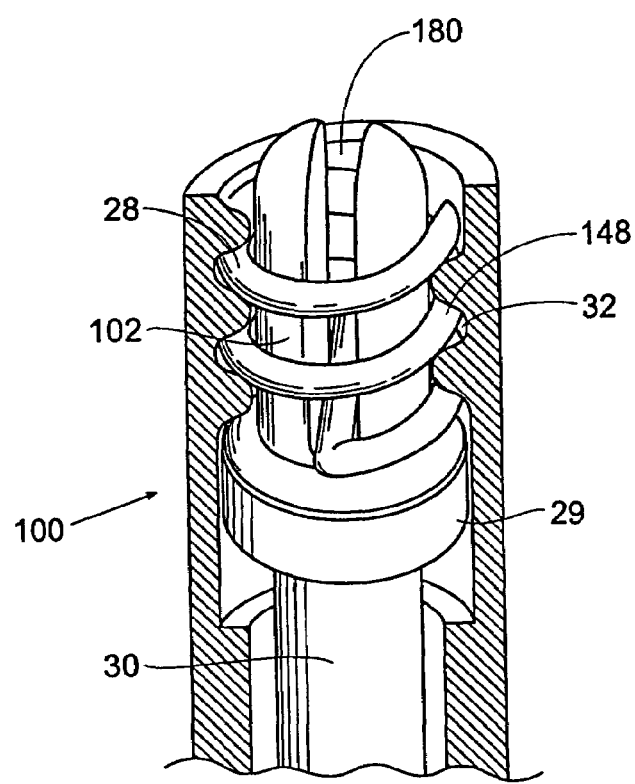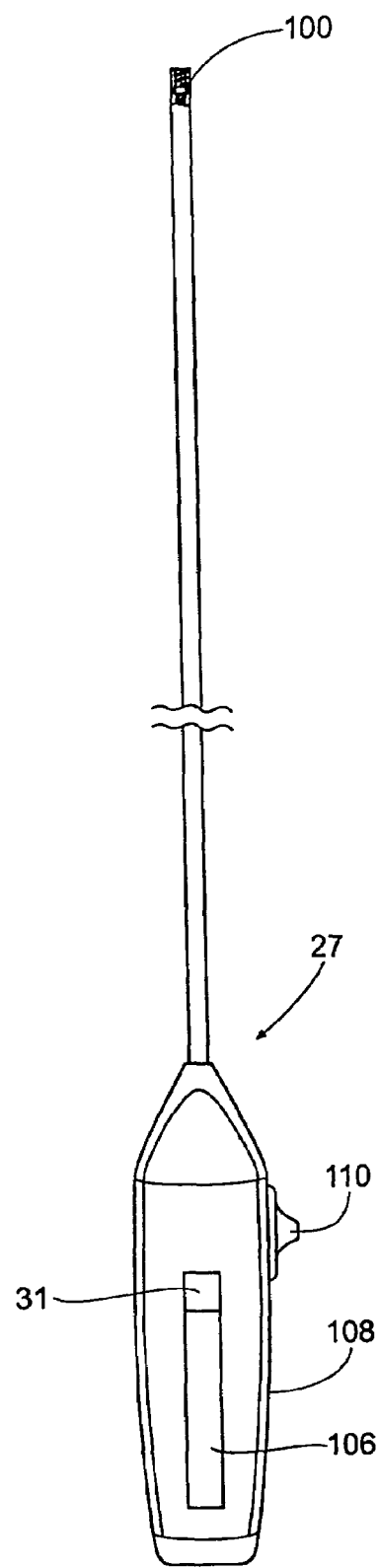
Fig. 14A
Fig. 14

CATHETER-BASED FASTENER IMPLANTATION APPARATUS AND METHODS WITH IMPLANTATION FORCE RESOLUTION

RELATED APPLICATIONS

This application is a continuation-in-part of co-pending U.S. patent application Ser. No. 10/307,226, filed Nov. 29, 2002, entitled "Intraluminal Prosthesis Attachment Systems and Methods." This application is also a continuation-in-part of U.S. patent application Ser. No. 10/271,334, filed Oct. 15, 2002, now U.S. Pat. No. 6,960,217, entitled "Endovascular Aneurysm Repair System," which claims the benefit of U.S. Provisional Application Ser. No. 60/333,937, filed Nov. 28, 2001. This application is also a continuation-in-part of U.S. patent application Ser. No. 10/099,149, filed Mar. 15, 2002, now U.S. Pat. No. 6,800,081, entitled "Systems and Methods for Applying a Suture within a Blood Vessel Lumen", which is a divisional of U.S. patent application Ser. No. 09/787,135, filed Jun. 4, 2001, entitled "Endovascular Fastener Applicator," now U.S. Pat. No. 6,592,593, which claims the benefit of U.S. Provisional Application Ser. No. 60/101,050 filed Sep. 18, 1998.

FIELD OF THE INVENTION

The invention relates generally to the delivery of a prosthesis to a targeted site within the body, e.g., for the repair of diseased and/or damaged sections of a hollow body organ and/or blood vessel.

BACKGROUND OF THE INVENTION

The weakening of a vessel wall from damage or disease can lead to vessel dilatation and the formation of an aneurysm. Left untreated, an aneurysm can grow in size and may eventually rupture.

For example, aneurysms of the aorta primarily occur in abdominal region, usually in the infrarenal area between the renal arteries and the aortic bifurcation. Aneurysms can also occur in the thoracic region between the aortic arch and renal arteries. The rupture of an aortic aneurysm results in massive hemorrhaging and has a high rate of mortality.

Open surgical replacement of a diseased or damaged section of vessel can eliminate the risk of vessel rupture. In this procedure, the diseased or damaged section of vessel is removed and a prosthetic graft, made either in a straight of bifurcated configuration, is installed and then permanently attached and sealed to the ends of the native vessel by suture. The prosthetic grafts for these procedures are usually unsupported woven tubes and are typically made from polyester, ePTFE or other suitable materials. The grafts are longitudinally unsupported so they can accommodate changes in the morphology of the aneurysm and native vessel. However, these procedures require a large surgical incision and have a high rate of morbidity and mortality. In addition, many patients are unsuitable for this type of major surgery due to other co-morbidities.

Endovascular aneurysm repair has been introduced to overcome the problems associated with open surgical repair. The aneurysm is bridged with a vascular prosthesis, which is placed intraluminally. Typically these prosthetic grafts for aortic aneurysms are delivered collapsed on a catheter through the femoral artery. These grafts are usually designed with a fabric material attached to a metallic scaffolding (stent) structure, which expands or is expanded to contact the internal diameter of the vessel. Unlike open surgical aneurysm repair, intraluminally deployed grafts are not sutured to the native vessel, but rely on either barbs extending from the stent, which penetrate into the native vessel during deployment, or the radial expansion force of the stent itself is utilized to hold the graft in position. These graft attachment means do not provide the same level of attachment when compared to suture and can damage the native vessel upon deployment.

SUMMARY OF THE INVENTION

One aspect of the invention provides apparatus and methods for implanting a fastener in a targeted body region, e.g., within a hollow body organ or an intraluminal space. The apparatus and methods deploy into the targeted body region a fastener attachment assembly that includes an actuated member. The actuated member is selectively operable to generate an implantation force to implant a fastener into tissue within the targeted body region. The fastener can be implanted, e.g., to secure a prosthesis. The prosthesis can comprise, e.g., an endovascular graft, which can be deployed without damaging the native blood vessel in either an arterial or a venous system. The endovascular graft can comprise, e.g., a radially expanding vascular stent and/or a stent-graft. The graft can be placed in the vasculature, e.g., to exclude or bridge an aneurysm, for example, an abdominal aortic aneurysm. The graft desirably adapts to changes in aneurysm morphology and repairs the endovascular aneurysm. The fastening apparatus and methods can be deployed through the vasculature and manipulated from outside the body, to deliver a fastener to attach the graft to the vessel wall.

According to this aspect of the invention, the systems and apparatus apply a resolution force to counteract or oppose some or all or a substantial portion of the implantation force. It is desirable to resolve some or all or a substantial portion of the implantation force within the vessel lumen (or other hollow body organ) itself, and preferably as close to the implantation site as possible, thereby making possible a stable and dependable catheter-based fastening platform.

In one embodiment, the resolution force comprises a substantially equal and opposite counteracting force to a location on the wall of the vessel or hollow body organ, desirably generally opposite to the implantation site.

In one embodiment, the actuated member comprises a driven member for implanting a helical fastener. However, the actuated member can comprise any mechanism for exerting an implantation force using, e.g., ultrasonic, laser, or impact concepts.

In one embodiment, the systems and methods includes a directing component and a fastener applier component. The directing component directs and/or positions the fastener applier component at or near the desired implant location. In this arrangement, the directing component can include means to stabilize the position the directing component, thereby providing a resolution force, and/or the directing component can be sized and configured to itself provide a sufficient resolution force with or without additional stabilization means. In another arrangement, the fastener applier component can be sized and configured to itself provide a sufficient resolution force with or without additional stabilization means, and with or without a resolution force contributed by the directing component.

In one embodiment, the stabilizion means can include expandable members, membranes, linkages and/or other mechanical systems to stabilize the directing component within the hollow body organ or vessel. The stabilization means can also include means to grasp and/or anchor to the wall of the hollow body organ, vessel or prosthesis prior to implanting a fastener. The grasping or anchoring means can include penetrating needles and/or hooks or barbs.

In one embodiment, the stabilization means can be associated with the fastener applier component instead of or in combination with stabilization means associated with the directing component.

In one embodiment, the stabilization means can take the form of a stabilization device separate from the directing component and applier component. In this arrangement, the separate stabilization device is used in cooperation with the directing component and/or the fastener applier component.

BRIEF DESCRIPTION OF THE DRAWINGS

The invention will be understood from the following detailed description of preferred embodiments, taken in conjunction with the accompanying drawings, wherein:

FIG. 14 is one embodiment of the fastener applier;

FIG. 14A is an enlarged view of the distal end of the fastener applier shown in FIG. 14, showing the details of the fastener drive mechanism;

DETAILED DESCRIPTION OF THE INVENTION

I. Delivering a Prosthesis

Figure 1:
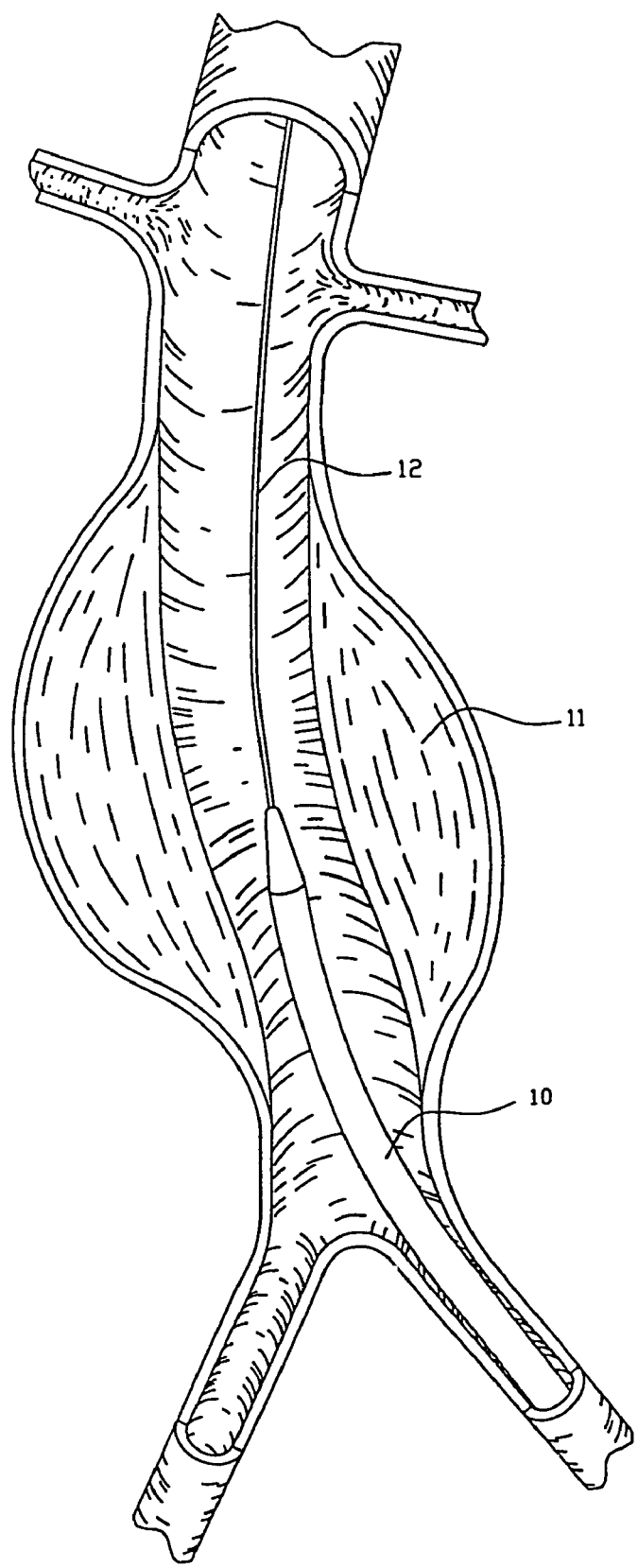
FIG. 1 is a perspective view of one embodiment of an endovascular graft delivery device shown positioned within an abdominal aortic aneurysm.

FIG. 1 depicts an endovascular graft delivery catheter 10 as it is being positioned over a guidewire 12 in a body lumen. The catheter 10 carries a prosthesis 14 (see FIG. 2), which is placed at a targeted site, e.g., by radial expansion of the prosthesis 14 (see FIG. 3). After partial or complete expansion of the prosthesis 14, one or more fasteners 28 (see FIGS. 15 and 16) are introduced by a fastener attachment assembly (as will be described in greater detail later) to anchor the prosthesis 14 in place.

For the purposes of illustration, FIG. 1 shows the targeted site as being within an abdominal aortic aneurysm 11. The targeted site can be elsewhere in the body. In the illustrated arrangement, the prosthesis 14 takes the form of an endovascular graft.

Figure 2:
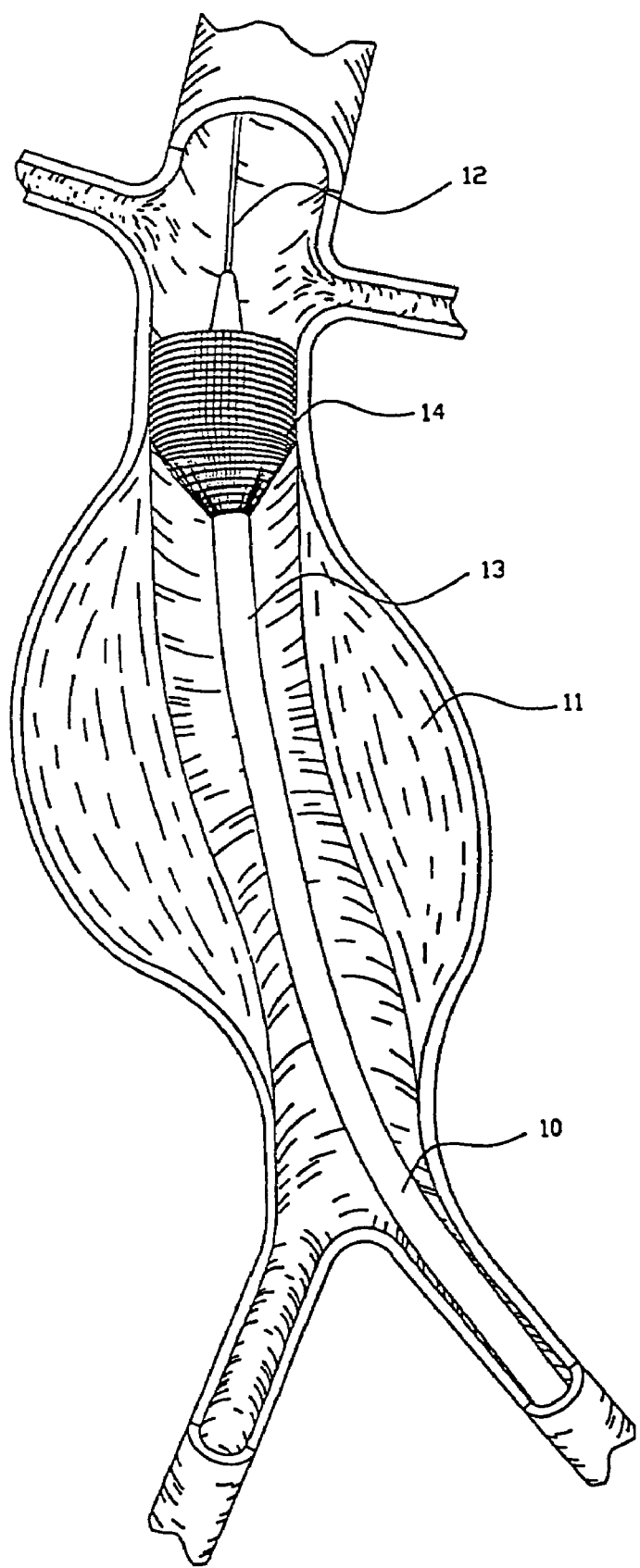
FIG. 2 is a perspective view of one embodiment the deployment of an endovascular graft within the aneurysm of FIG. 1.

FIG. 2 depicts the initial stage of graft deployment at the targeted site. While the deployment method can vary, in the illustrated embodiment, the delivery catheter 10 has a movable cover 13, which overlays the graft 14. When the cover 13 is pulled proximally, the graft 14 is free to radially expand, thereby enlarging to contact the internal walls of the blood vessel. The graft 14 is shown to be self-expanding. Alternatively, the graft 14 can utilize an expanding member, such as a balloon or mechanical expander.

Figure 3:
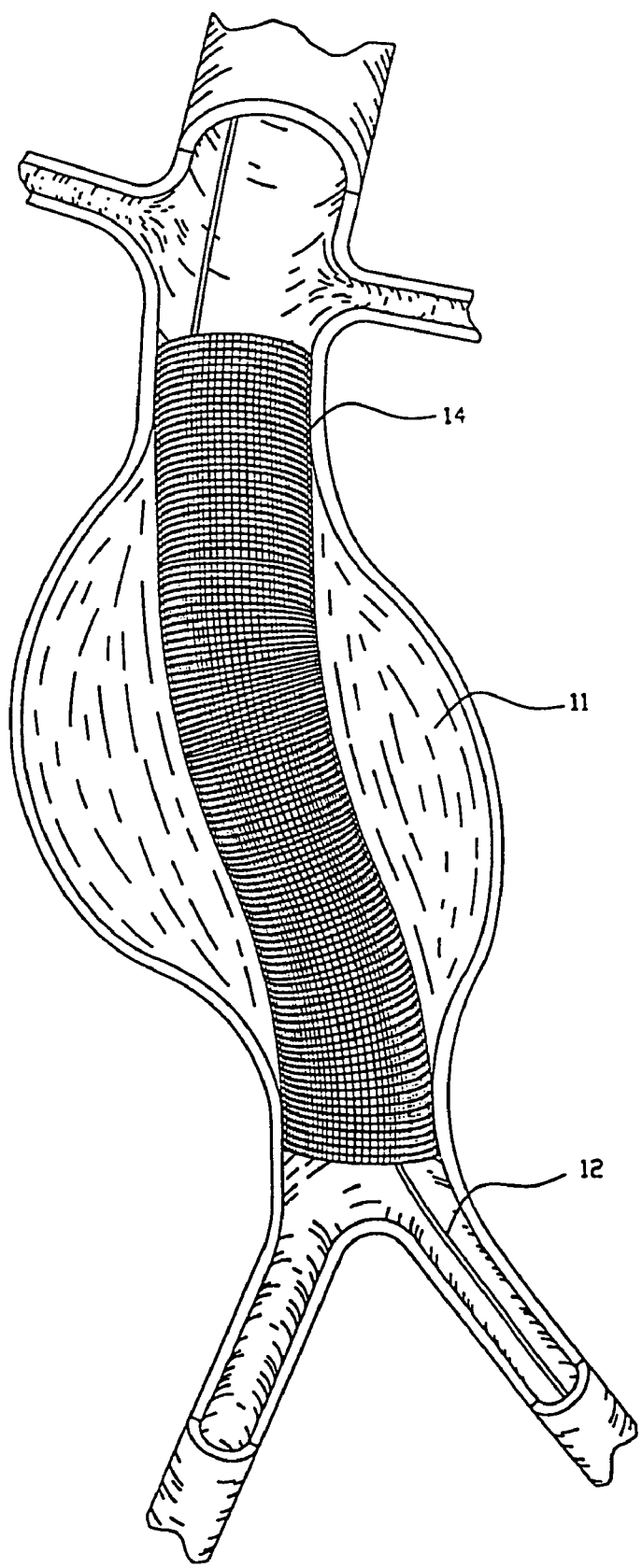
FIG. 3 is a perspective view of a fully deployed straight endovascular graft of FIG. 2.
Figure 4:
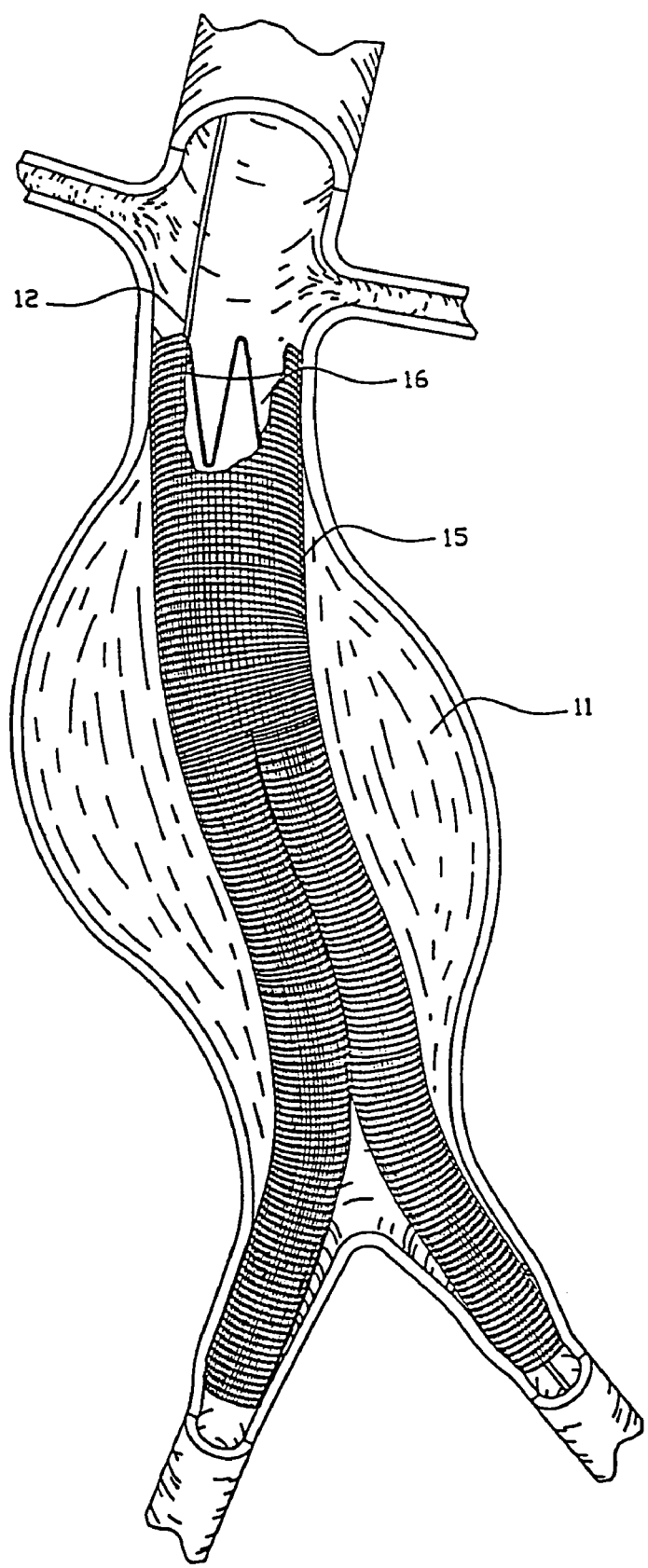
FIG. 4 is a perspective view of a fully deployed bifurcated endovascular graft broken away to show an anchoring scaffold at one end.

The process of graft deployment is continued, until the graft 14 is fully deployed or partially deployed within the vessel. The graft 14 can be sized and configured to be either straight or bifurcated form. FIG. 3 depicts a completely deployed straight graft 14. FIG. 4 depicts a completely deployed bifurcated graft 15.

A. The Prosthesis

The graft 14 desirably incorporates a support frame or scaffold 16. The scaffold 16 may be elastic, e.g., comprised of a shape memory alloy elastic stainless steel, or the like. For elastic scaffolds, expanding typically comprises releasing the scaffolding from a constraint to permit the scaffold to self-expand at the implantation site. In the illustrated arrangement, the cover 13 serves as a radial constraint. Alternatively, placement of a tubular catheter, delivery sheath, or the like over the scaffold 16 can serve to maintain the scaffold in a radially reduced configuration. In this arrangement, self-expansion of the scaffold 16 is achieved by pulling back on the radial constraining member, to permit the scaffold 16 to assume its larger diameter configuration.

Alternatively, the scaffold 16 may be constrained in an axially elongated configuration, e.g., by attaching either end of the scaffold to an internal tube, rod, catheter or the like. This maintains the scaffold 16 in the elongated, reduced diameter configuration. The scaffold 16 may then be released from such axial constraint in order to permit self-expansion.

Alternatively, the scaffold 16 may be formed from a malleable material, such as malleable stainless steel of other metals. Expansion may then comprise applying a radially expansive force within the scaffold to cause expansion, e.g., inflating a scaffold delivery catheter within the scaffold in order to affect the expansion. In this arrangement, the positioning and deployment of the endograft can be accomplished by the use of an expansion means either separate or incorporated into the deployment catheter. This will allow the endograft to be positioned within the vessel and partially deployed while checking relative position within the vessel. The expansion can be accomplished either via a balloon or mechanical expansion device. Additionally, this expansion stabilizes the position of the endograft within the artery by resisting the force of blood on the endograft until the endograft can be fully deployed.

The graft 14 may have a wide variety of conventional configurations. It can typically comprise a fabric or some other blood semi-impermeable flexible barrier which is supported by the scaffold 16, which can take the form of a stent structure. The stent structure can have any conventional stent configuration, such as zigzag, serpentine, expanding diamond, or combinations thereof. The stent structure may extend the entire length of the graft, and in some instances can be longer than the fabric components of the graft. Alternatively, the stent structure can cover only a small portion of the prosthesis, e.g., being present at the ends. The stent structure may have three or more ends when it is configured to treat bifurcated vascular regions, such as the treatment of abdominal aortic aneurysms, when the stent graft extends into the iliac arteries. In certain instances, the stent structures can be spaced apart along the entire length, or at least a major portion of the entire length, of the stent-graft, where individual stent structures are not connected to each other directly, but rather connected to the fabric or other flexible component of the graft.

One illustrative embodiment of the graft scaffold 16 or stent structure is illustrated in the area broke away in FIG. 4.

Figure 5:
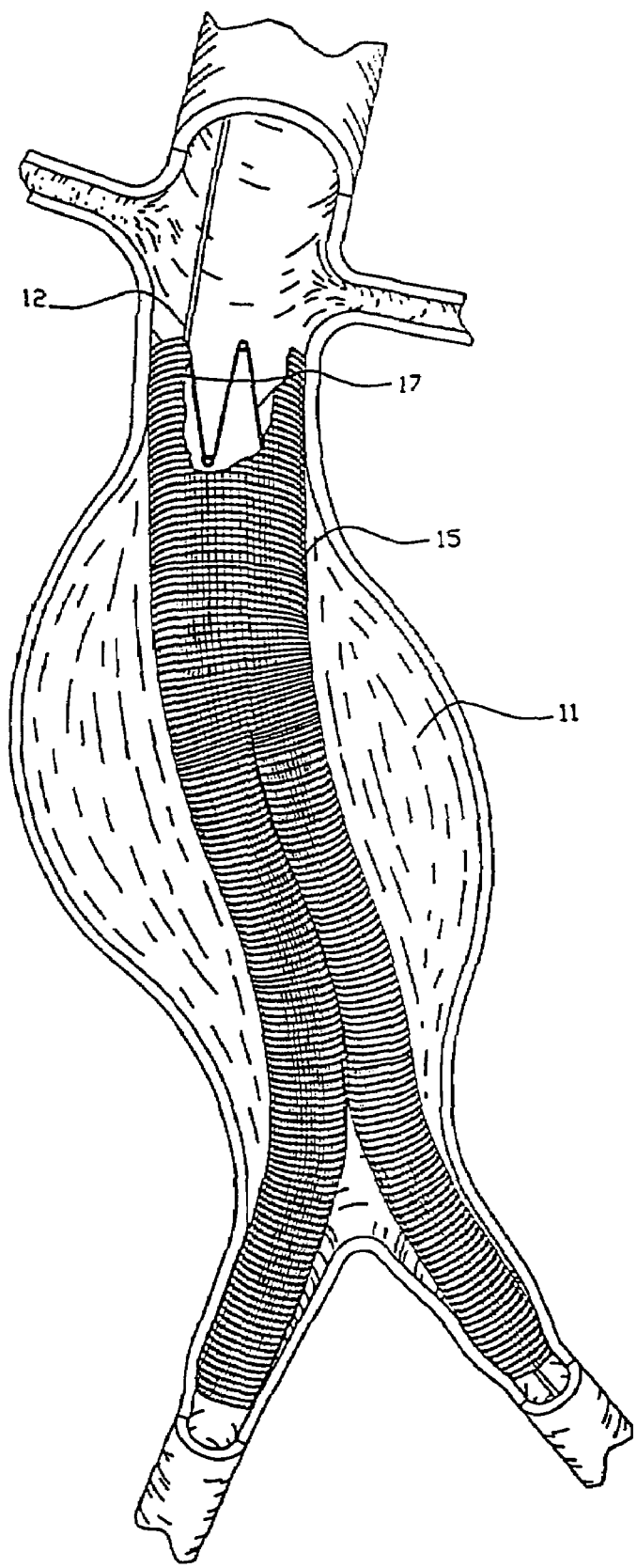
FIG. 5 is a perspective view similar to FIG. 5 showing an alternative scaffold structure.

Here, the stent structure is in the form of a simple zigzag pattern, however it is contemplated that the stent design could involve more complex patterns 17 as depicted in FIG. 5. Although only one stent structure within the graft is depicted, in FIGS. 4 and 5, it is contemplated that multiple independent stent structures could be incorporated into the graft, as previously described.

Figure 40:
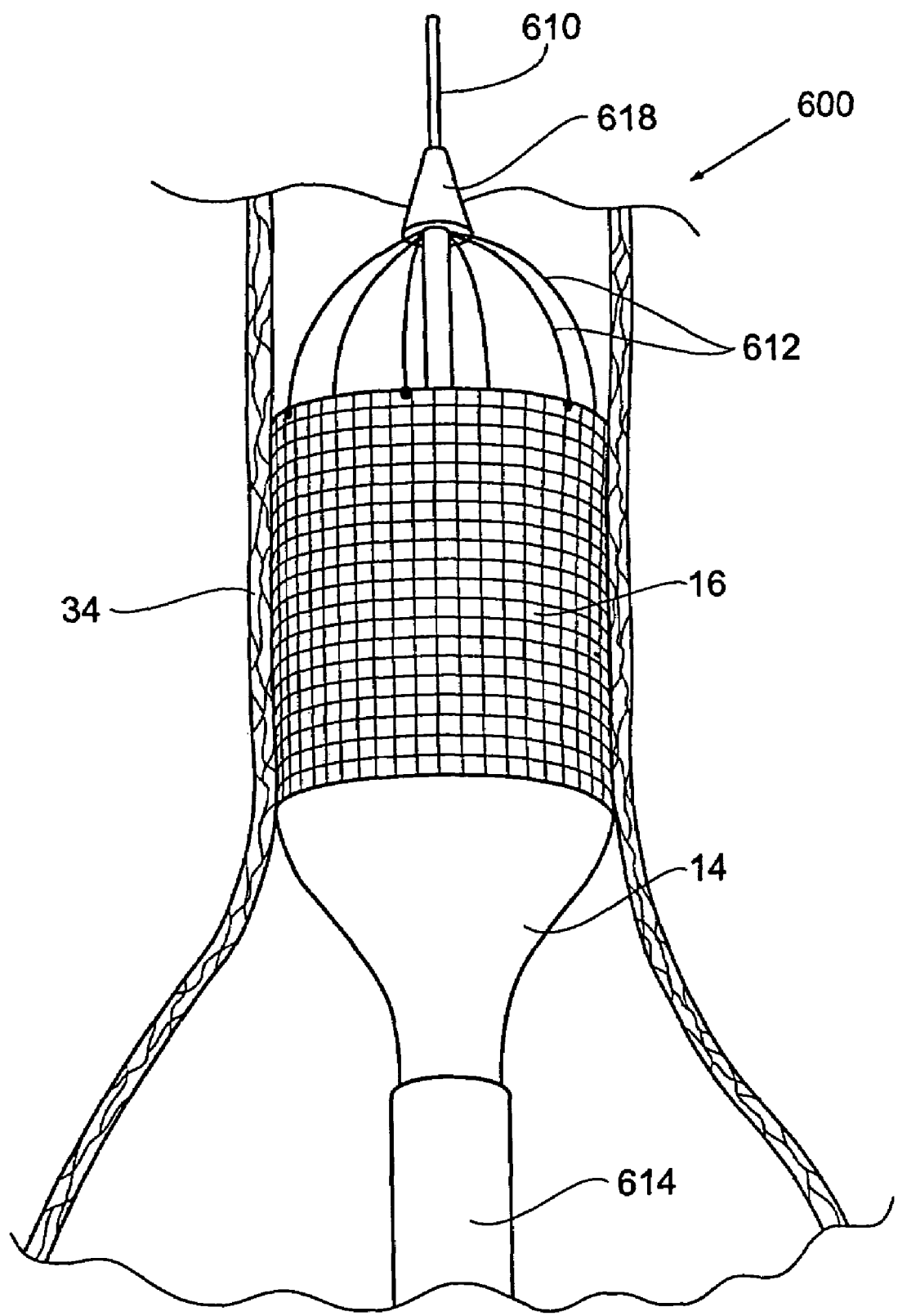
FIG. 40 is an embodiment of a prosthesis delivery catheter for a prostheses in which the stent structure covers only a portion of the prosthesis, the catheter including an array of stabilization struts to help hold the prosthesis in position against the flow of blood.

FIG. 40 shows an embodiment of a prosthesis delivery catheter 600 for a prostheses 14 in which the stent structure 16 covers only a portion of the prosthesis, e.g., being present only at the ends. As shown in FIG. 40, the prosthesis delivery catheter 600 (which is shown deployed over a guidewire 610) includes an array of stabilization struts 612 that are releasably coupled to the stent structure 16 at the end of the prosthesis 14, e.g., by sutures that can be released by pulling on a drawstring (not shown) that passes through a lumen in the catheter 600. The stabilization struts 612 hold the self-expanding stent structure 16 in position against the vessel wall 34, while the remainder of the prosthesis 14 is being deployed (by withdrawal of a delivery sheath 614). The struts 612 support the stent structure 16 (and thus the overall prosthesis 14) against the force of blood flow through the vessel during prosthesis deployment. The catheter 600 can also include a nose cone 618 at its distal end to diffuse blood flow toward the vessel wall, to aid in supporting the prosthesis 14 during its deployment. Upon deployment of the prosthesis 14, the struts 612 can be detached from the stent structure 14 by pulling upon the drawstring to release the sutures, and the catheter 600 is withdrawn over the guidewire 610 through the delivery sheath 614 (the struts 612, freed from the stent structure 16, fold back upon the catheter 600 during passage through the delivery sheath 614).

Figure 41:
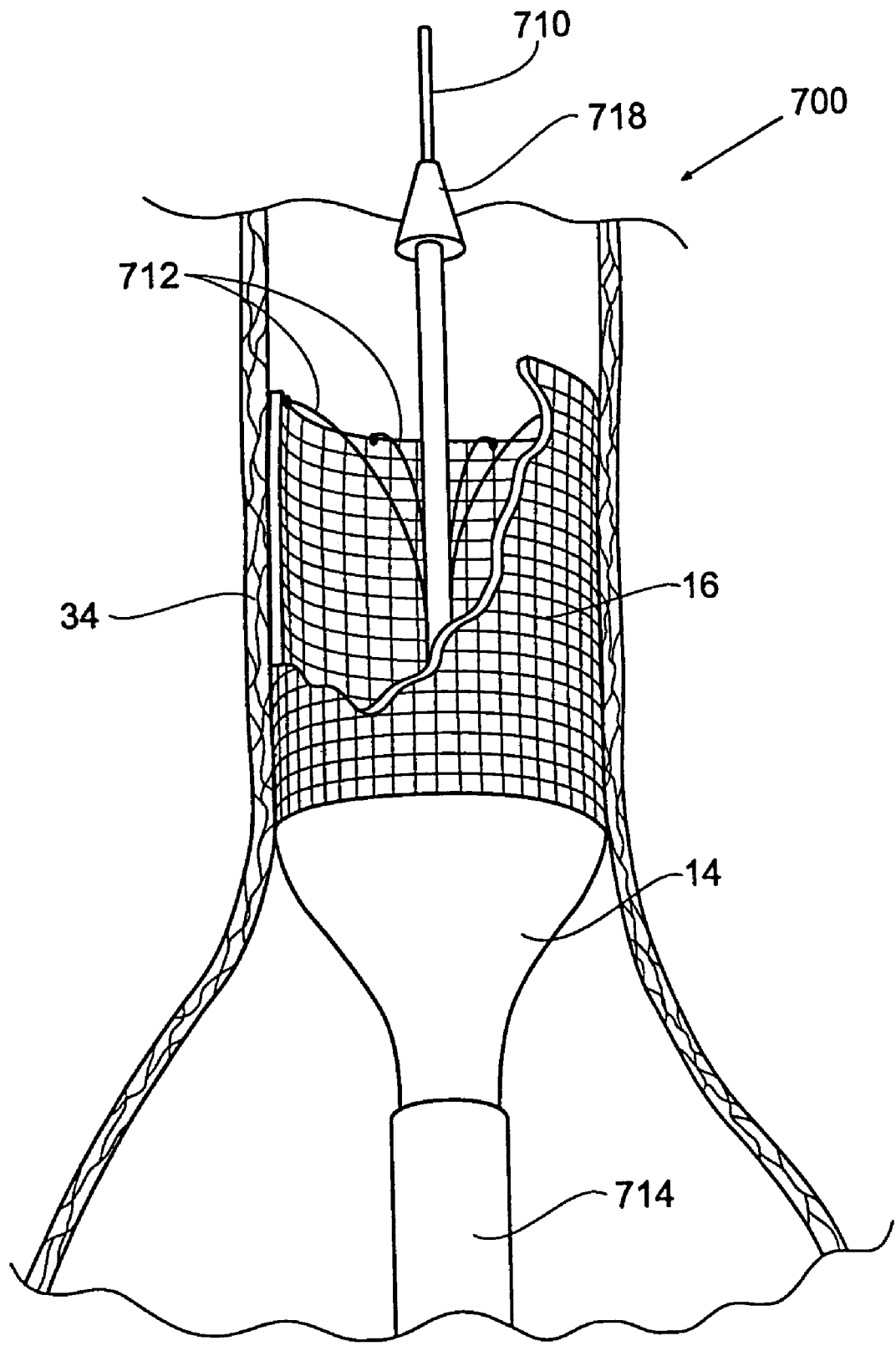
FIG. 41 is another embodiment of a prosthesis delivery catheter for a prostheses in which the stent structure covers only a portion of the prosthesis, the catheter including an array of inverted stabilization struts to help hold the prosthesis in position against the flow of blood.

FIG. 41 shows an alternative embodiment of a prosthesis delivery catheter 700 for a prostheses 14 in which the stent structure 16 covers only a portion of the prosthesis, e.g., being present at the ends. As shown in FIG. 40, the prosthesis delivery catheter 700 (which is also shown deployed over a guidewire 710) includes an array of inverted stabilization struts 712 that are releasably coupled to the stent structure 16 at the end of the prosthesis 14, e.g., by sutures that can be released by pulling on a drawstring (not shown) that passes through a lumen in the catheter 700. The inverted stabilization struts 712, like the struts 612 shown in FIG. 40, hold the self-expanding stent structure 16 in position against the vessel wall 34, while the remainder of the prosthesis 14 is being deployed (by withdrawal of a delivery sheath 714). Like the catheter 600 in FIG. 40, the catheter 700 can also include a nose cone 718 at its distal end to diffuse blood flow toward the vessel wall. Upon deployment of the prosthesis 14, the struts 712 are detached from the stent structure 14 by pulling upon the drawstring not shown), and the catheter 700 is withdrawn over the guidewire 710 through the delivery sheath 714 (the struts 612, freed from the stent structure 16, fold back upon the catheter 600 during passage through the delivery sheath 614).

Figure 42:
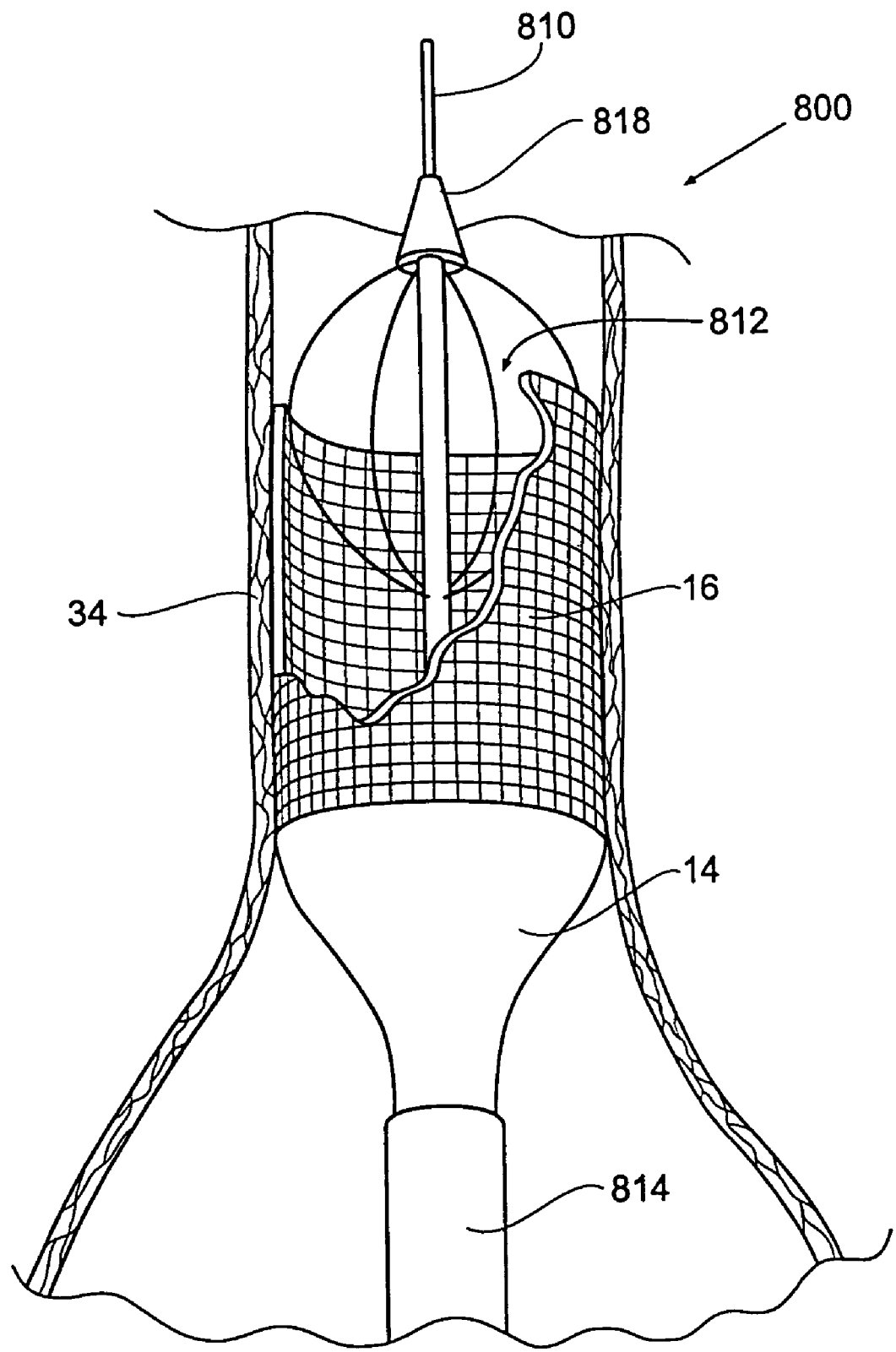
FIG. 42 is another embodiment of a prosthesis delivery catheter for a prostheses in which the stent structure covers only a portion of the prosthesis, the catheter including a stabilization basket to help hold the prosthesis in position against the flow of blood.

FIG. 42 shows another alternative embodiment of a prosthesis delivery catheter 800 for a prostheses 14 in which the stent structure 16 covers only a portion of the prosthesis, e.g., being present at the ends. As shown in FIG. 42, the prosthesis delivery catheter 800 (which is also shown deployed over a guidewire 810) includes a self-expanding stabilization basket 812. The stabilization basket 812 holds the self-expanding stent structure 16 in position against the vessel wall, while the remainder of the prosthesis 14 is being deployed (by withdrawal of a delivery sheath 814). Like the catheters 600 and 700 in FIGS. 40 and 41, the catheter 800 can also include a nose cone 818 at its distal end to diffuse blood flow toward the vessel wall. Upon complete deployment of the prosthesis 14, the stabilization basket can be placed into a collapsed condition by withdrawal through the delivery sheath 814, as the catheter 800 is withdrawn over the guidewire 810.

In all of the just-described embodiments, if the prosthesis 14 has been fully deployed prior to the introduction of the fasteners 28, and/or the prosthesis delivery catheter 600, 700, or 800 has been withdrawn from the targeted site, the guidewire 610, 710, 810 can be subsequently used to deploy a fastener attachment assembly for the prosthesis 14 to the targeted site, as will be described in greater detail next. Alternatively, if the prosthesis 14 has not been fully deployed at the time the fasteners 28 are applied—or if, for whatever reason, withdrawal of the prosthesis delivery catheter 600, 700, or 800 is not desired—the prosthesis delivery catheter 600, 700, or 800, and its respective guidewire 610, 710, or 810, can be retained at the targeted site, while a fastener attachment assembly for the prosthesis 14 is introduced into the targeted site over a separate guidewire from another body access point. In this arrangement, deployment of the prosthesis 14 and/or withdrawal of the prosthesis delivery catheter 600, 700, or 800 can be completed after the fasteners 28 have been applied.

II. Fastening the Prosthesis

In a desired embodiment, a fastener attachment assembly is provided that makes possible intraluminal fastener attachment. The attachment assembly can be variously constructed.

A. Two Component Fastener Guide and Attachment Assembly

In one arrangement, the fastener attachment assembly comprises a fastener guide or directing component 18 and a fastener applier component 27. The guide component 18 desirably has a steerable or deflectable distal tip, which is initially deployed over the guidewire 12. In use in the illustrated embodiment, the guidewire 12 that is used to deliver and position the prosthesis 14 remains within the vessel for subsequent deployment of the fastener guide component 18. Alternatively, another guidewire from a different body access point can be used for deployment of the fastener guide component 18. In either arrangement, the fastener applier component 27 is desirably deployed through the guide component 18 after removal of the guidewire over which the guide component 18 has been delivered. The fastener applier 27 carries at least one fastener 28 and a fastener drive mechanism 100 for advancing the fastener 28, so that it penetrates the prosthesis 14 and underlying vessel wall, to thereby anchor the prosthesis 14 firmly in place.

1. Fastener Directing Component

Figure 6:
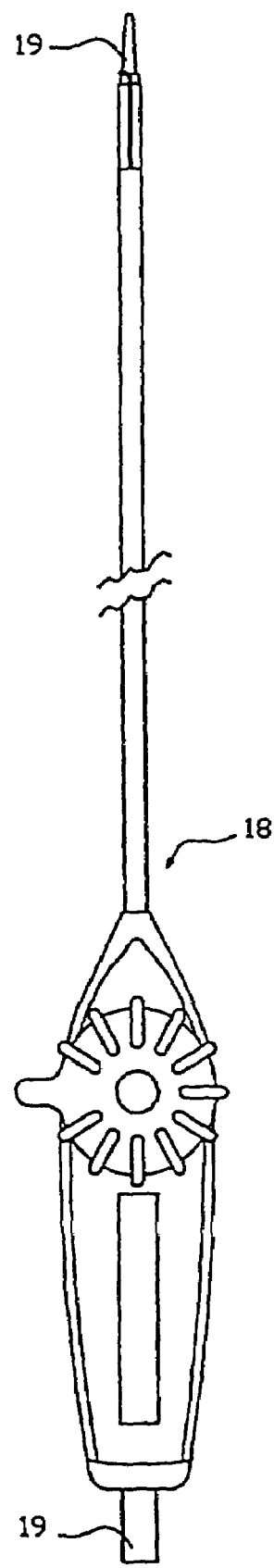
FIG. 6 is a perspective view showing one embodiment of a device for directing the fastener applier.
Figure 7:
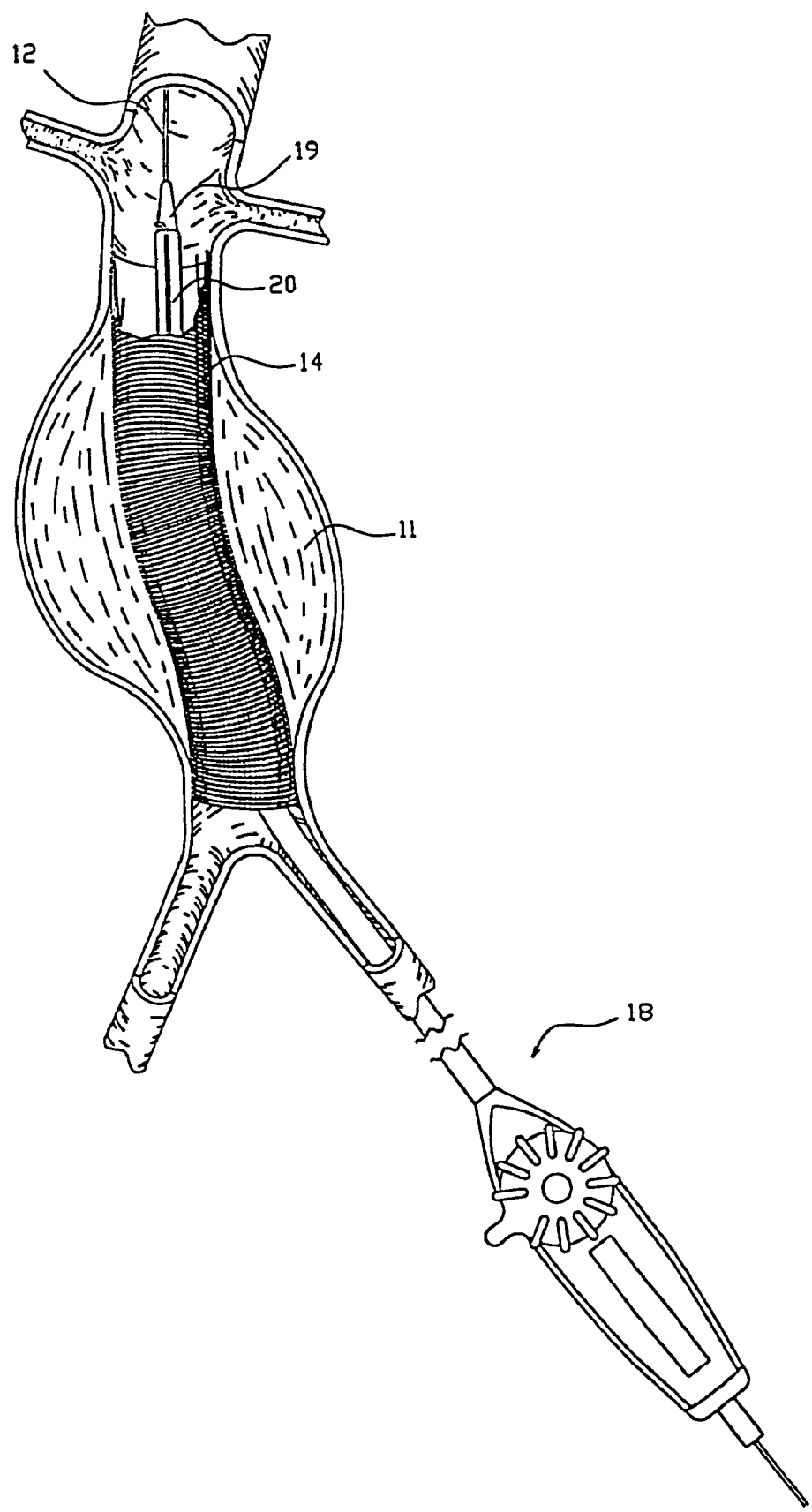
FIG. 7 is a perspective view showing the device of FIG. 6 upon insertion within the deployed endovascular graft of FIG. 3 with both the graft and scaffolding broken away.

FIG. 6 depicts one embodiment of the directing or guide component 18 that forms a part of the fastener attachment assembly. The component 18 includes an interior lumen that accommodates passage of an obturator 19. The obturator 19 has a lumen to allow for delivery of the directing component 18 over the guidewire 12, as shown in FIG. 7. Once deployed in a desired location, the obturator 19 and guidewire 12 are removed, leaving the central lumen open for passage of the fastener applier component 27, as will be described later.

Figure 8:
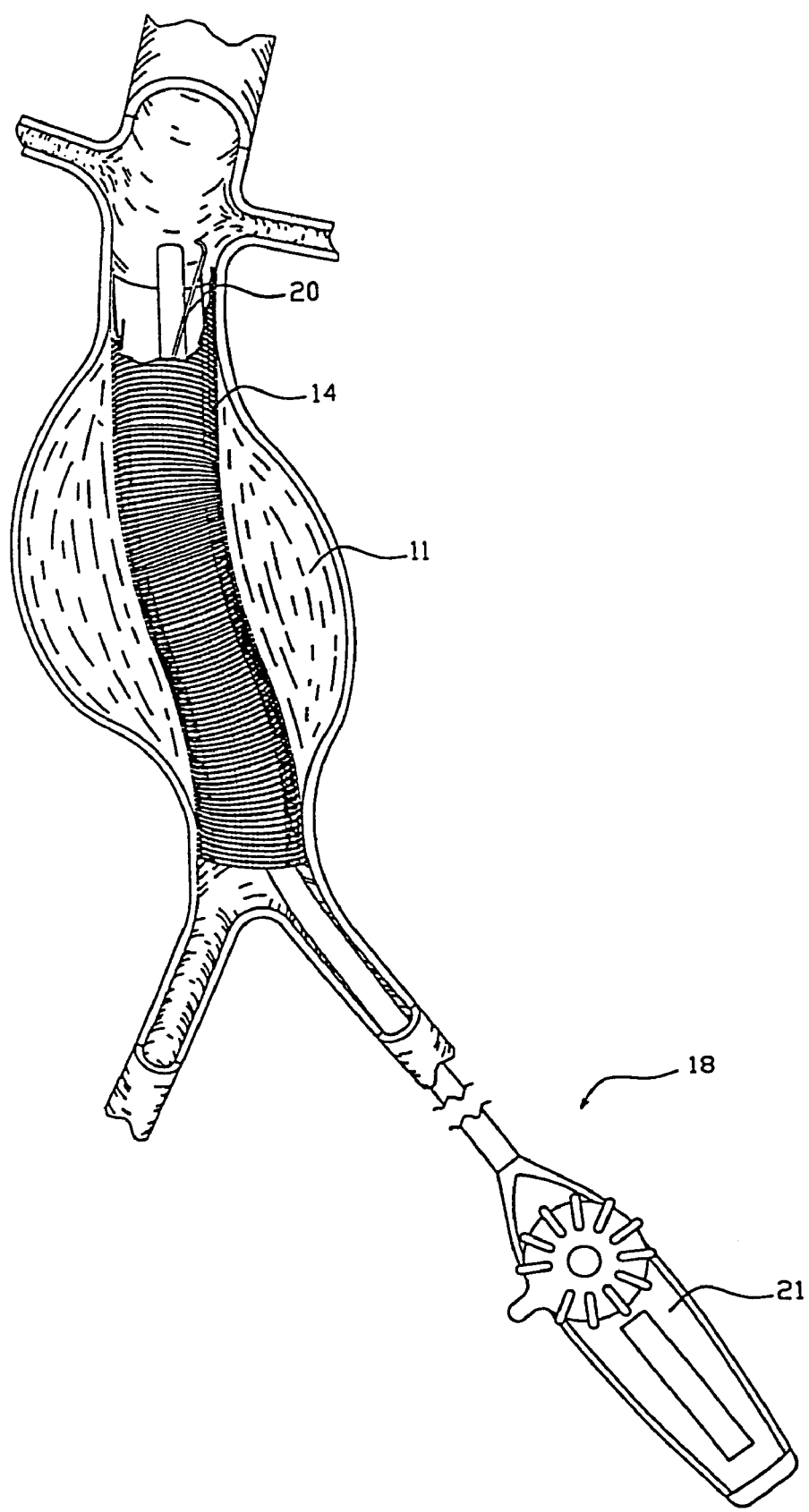
FIG. 8 is a perspective view of the device of FIG. 6 showing activation of one embodiment of a stabilizing device attached to the directing device.
Figure 9:
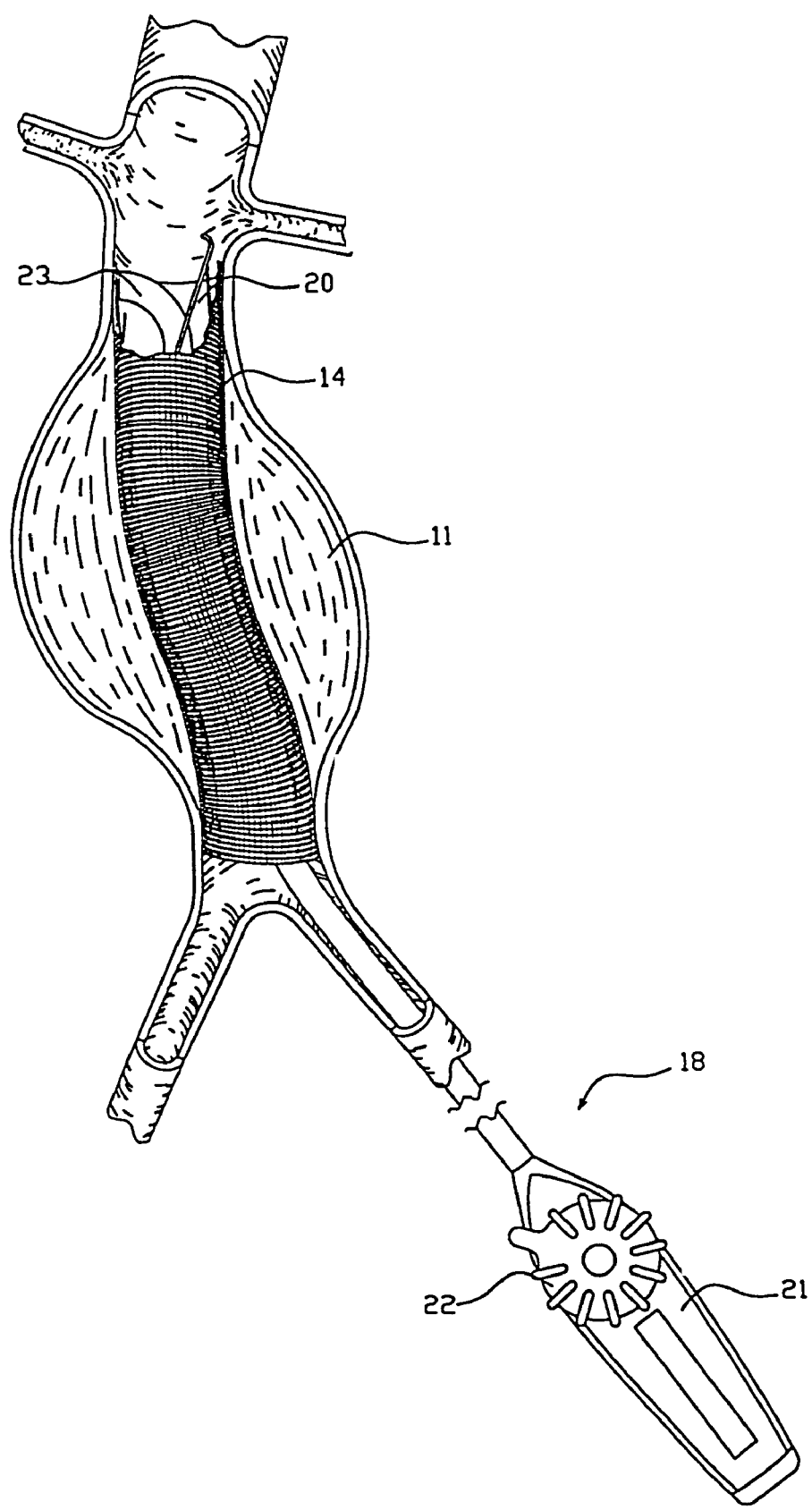
FIG. 9 is a perspective view of the control assembly in FIG. 8 articulating the directing device of FIG. 6.

In the illustrated embodiment (see FIG. 8), the directing component 18 includes a control assembly 21. In one embodiment the control assembly 21 features a movable wheel or lever 22, which operate interior steering wires in a conventional fashion to deflect the distal tip 23 of the directing component 18 toward a desired location, as seen in FIG. 9. It is contemplated that the control assembly 21 for the directing component 18 could be activated mechanically, electrically, hydraulically or pneumatically. The control assembly 21 has a through lumen to allow for the passage of the obturator 19 (as just described) and the fastener applier component 27, as will be described next.

2. Fastener Applier Component

FIG. 14 shows one embodiment of the fastener applier component 27 that forms a part of the fastener attachment assembly. As FIG. 15 depicts, the fastener applier component 27 is deployed through the central lumen of the directing component 18 to the site where a fastener 28 will be installed.

Located at the distal end of the fastener applier component 27 (see FIG. 14) is a fastener drive mechanism 100. In the illustrated embodiment (see FIG. 14A), the drive mechanism 100 includes a driver 29 that is coupled to a carrier 102. The coupling between the driver 29 and carrier 102 can take different forms—e.g., magnets, graspers, or other suitable mechanical connection. In the embodiment illustrated in FIG. 14A, the driver 29 and carrier 102 are integrally connected as a single unit.

Figure 18:
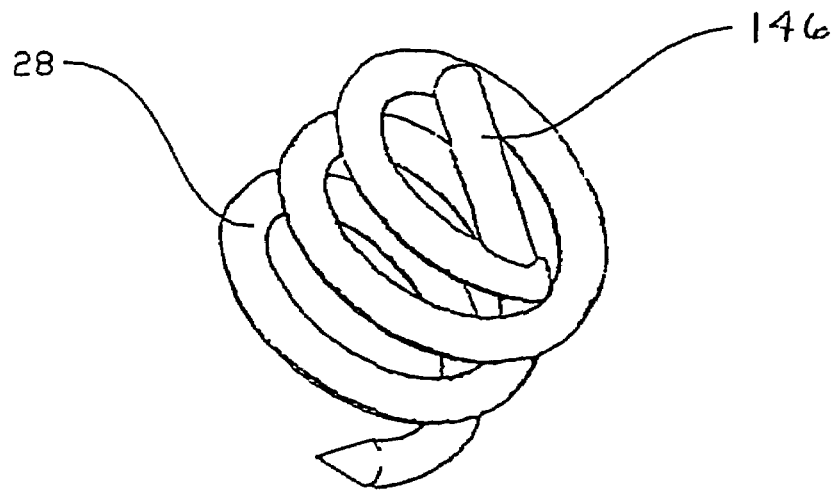
FIG. 18 is a enlarged perspective view of one embodiment of the helical fastener of FIG. 16.

The carrier 102 is sized and configured to engage a selected fastener 28. In FIG. 14A, the fastener takes the form of a helical fastener of the type shown in FIGS. 18 and 27. As best shown in FIG. 27, and as will be described in greater detail later, the helical fastener 28 in FIG. 26 is an open coil 148 with a sharpened leading tip 142. The proximal end 144 of the fastener 28 includes an L-shaped leg 146. The L-shape leg 146 desirably bisects the entire interior diameter of the coil 148; that is, the L-shaped leg 146 extends completely across the interior diameter of the coil 148, as FIG. 27 shows. The L-shaped leg 146 serves to engage the carrier 102 of the fastener applier 27, which rotates the helical fastener to achieve implantation. The L-shaped leg 146 also serves as a stop to prevent the helical fastener from penetrating too far into the tissue.

The carrier 102 in FIG. 14A includes a slot 180, which receives the L-shaped leg 146 to couple the fastener 28 for rotation with the carrier 102. The turns of the coil 148 rest in complementary internal grooves 32 that surround the carrier 102. The grooves 32 could be positioned along the entire length of the fastener 28 or within a portion of its length.

The actuation of the drive mechanism 100 can, of course, be accomplished in various ways, e.g., mechanical (i.e., manual or hand-powered), electrical, hydraulic, or pneumatic. In the illustrated embodiment (see FIG. 14B), a drive cable 30 couples the fastener driver 29 to an electric motor 106 carried in the applier handle 108. The drive cable 30 is desirably made of a suitable material that allows for both bending and rotation. Driven by the motor 106 (which is, in turn, under the control of motor control unit 31, as will be described later), the drive cable 30 rotates the driver 29 and, with it, the carrier 102. The carrier 102 imparts rotation and torque to the helical fastener 28 for implantation in tissue.

Figure 16:
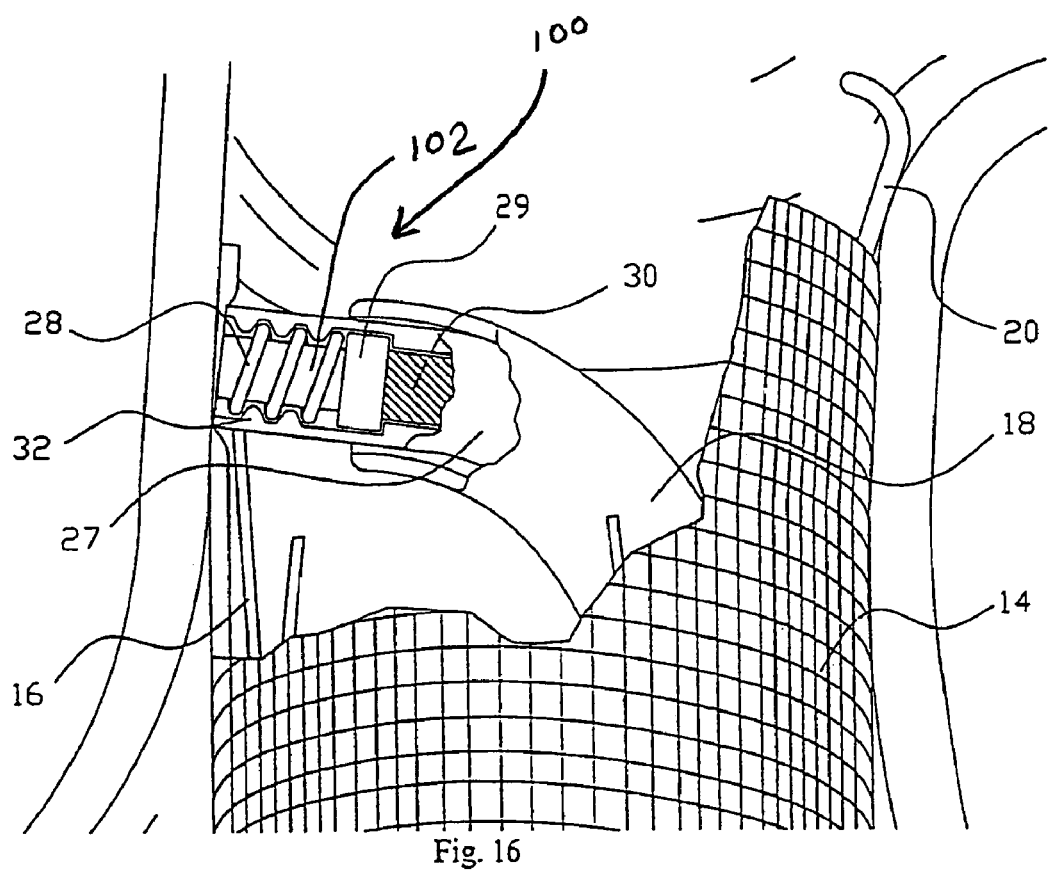
FIG. 16 is an enlarged cross-sectional view of one embodiment of the fastener applier of FIG. 14.
Figure 17:
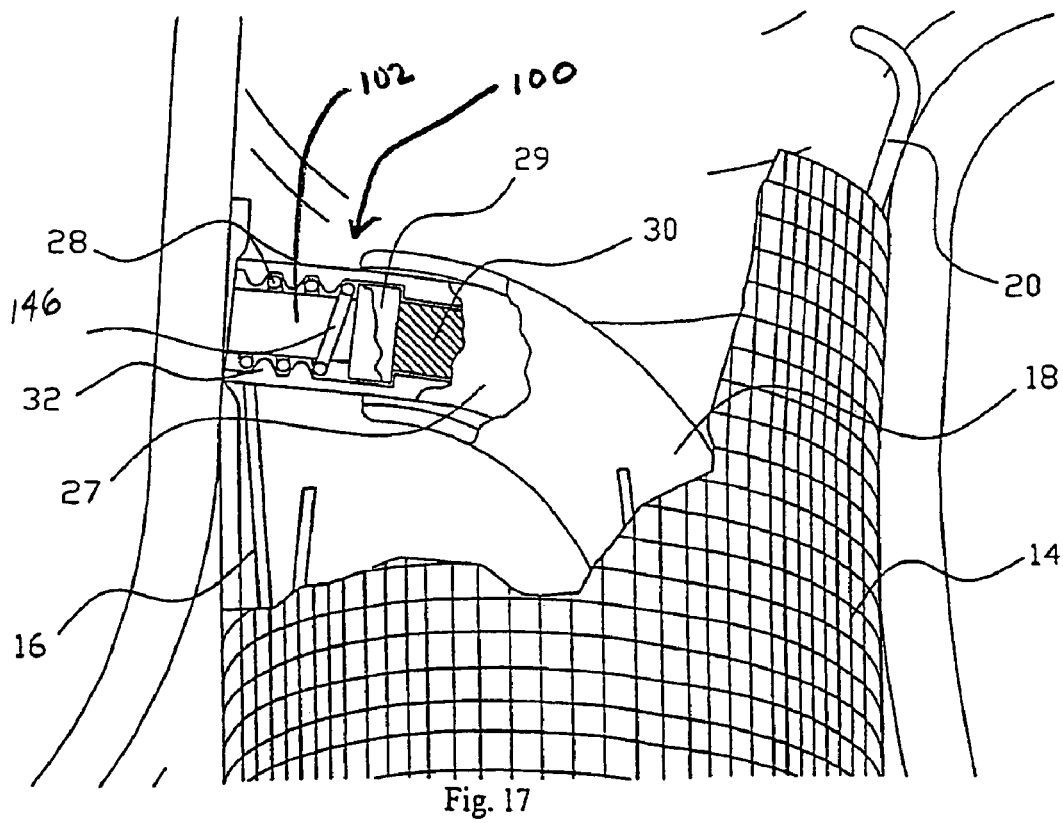
FIG. 17 is an enlarged cross-sectional view of the attachment applier showing one embodiment of the proximal end of the helical fastener and the drive mechanism.
Figure 19:
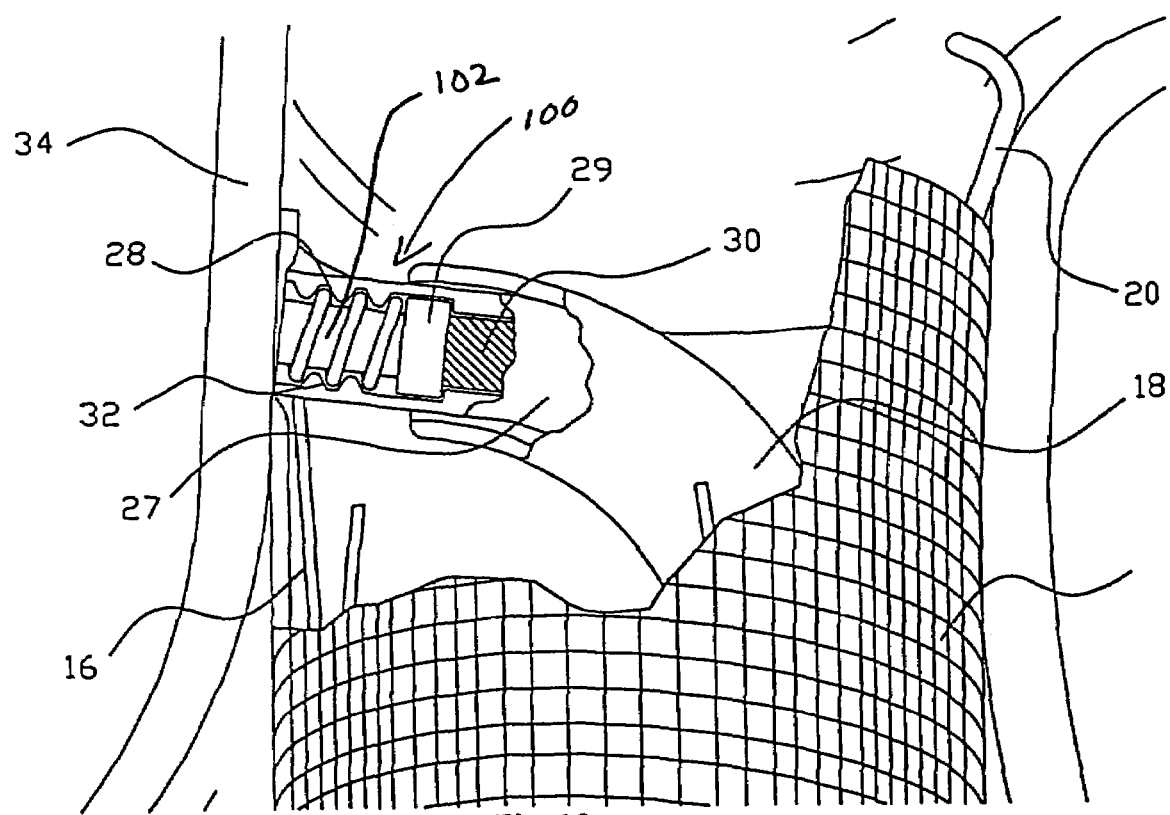
FIG. 19 is an enlarged view of the attachment applier showing one embodiment of the control assembly that activates the fastener applier.
Figure 20:
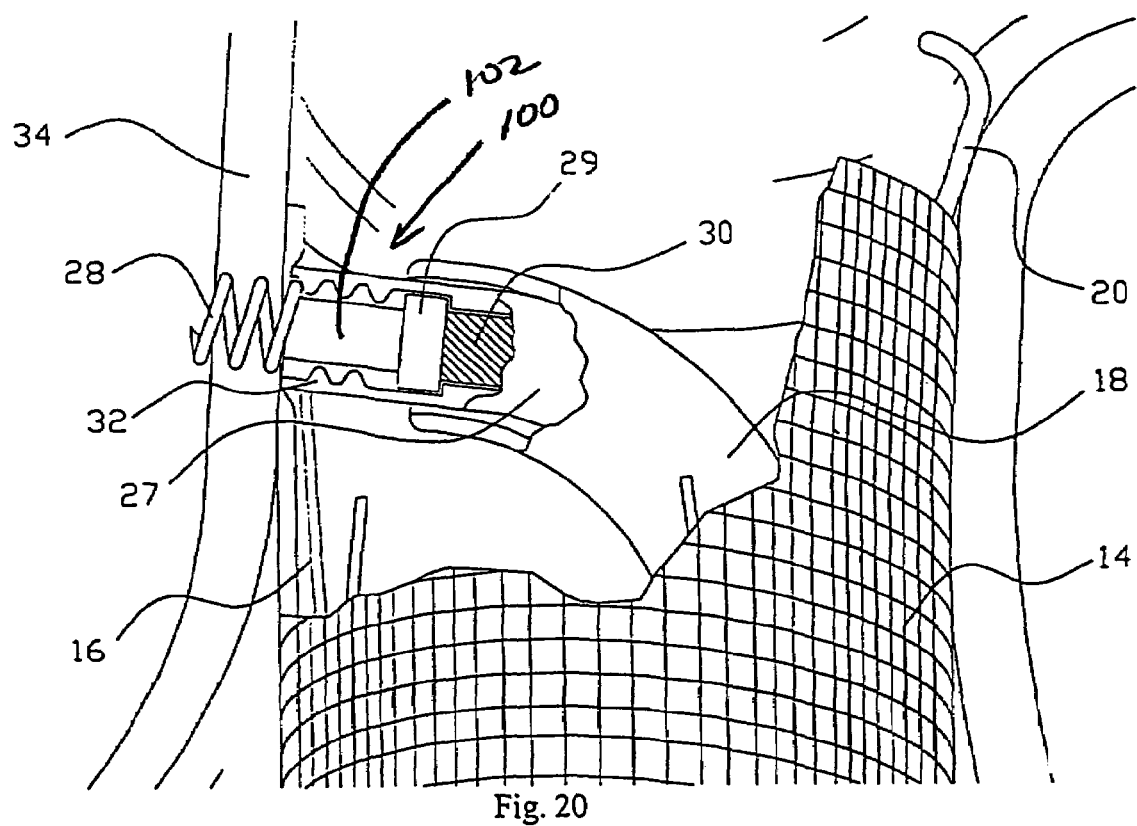
FIG. 20 is an enlarged view of the attachment applied activated with a fastener implanted into the graft and vessel wall.
Figure 21:
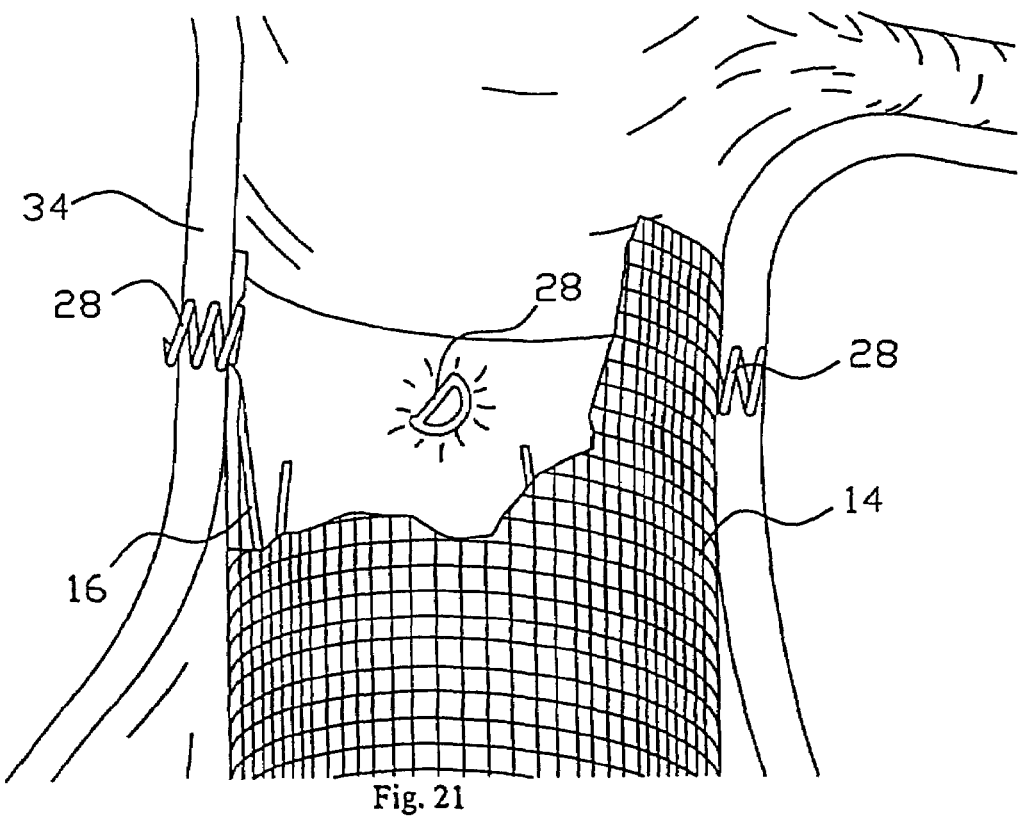
FIG. 21 is an enlarged view of the completed attachment of the proximal graft of FIG. 3 to the vessel wall with fasteners.

FIG. 16 is an enlarged cross-sectional view of fastener applier 27 and directing device 18. FIG. 17 is an enlarged cross-sectional view of the fastener applier 27 with a cross-section of the fastener driver 29 depicting the engagement between the fastener driver 29 and helical fastener 28. FIG. 19 depicts the fastener applier 27 during activation of the fastener drive mechanism 100. Activation of the drive mechanism 100 rotates, as a unit, the drive shaft 30, the driver 29, the carrier 102, and helical fastener 28. This rotation causes the helical fastener 28 to travel within the internal grooves 32 of the fastener applier and into the prosthesis 14 and vessel wall 34 (see FIG. 20). FIG. 21 illustrates a completed helical fastener 28 attachment of the graft 14 to the vessel wall 34.

In use, the applier component 27 is advanced through the directing component 18 and into contact with the prosthesis.

Figure 14B:
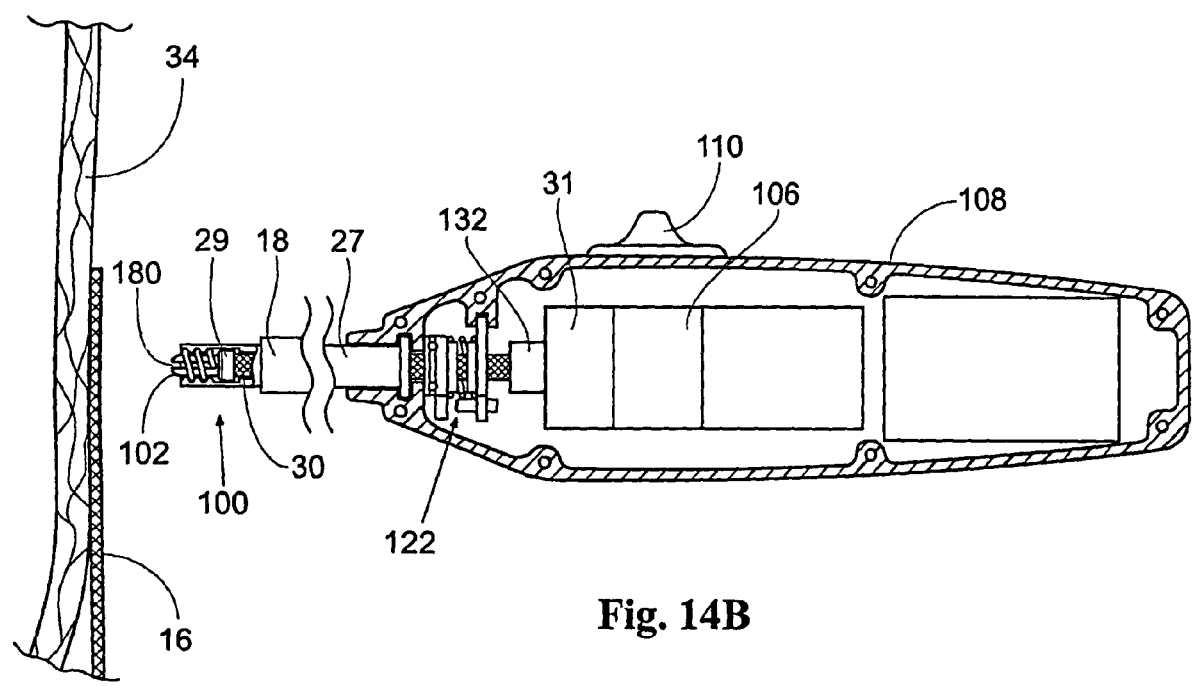
FIG. 14B is a section view of the interior of the handle of the fastener applier shown in FIG. 14.
Figure 15:
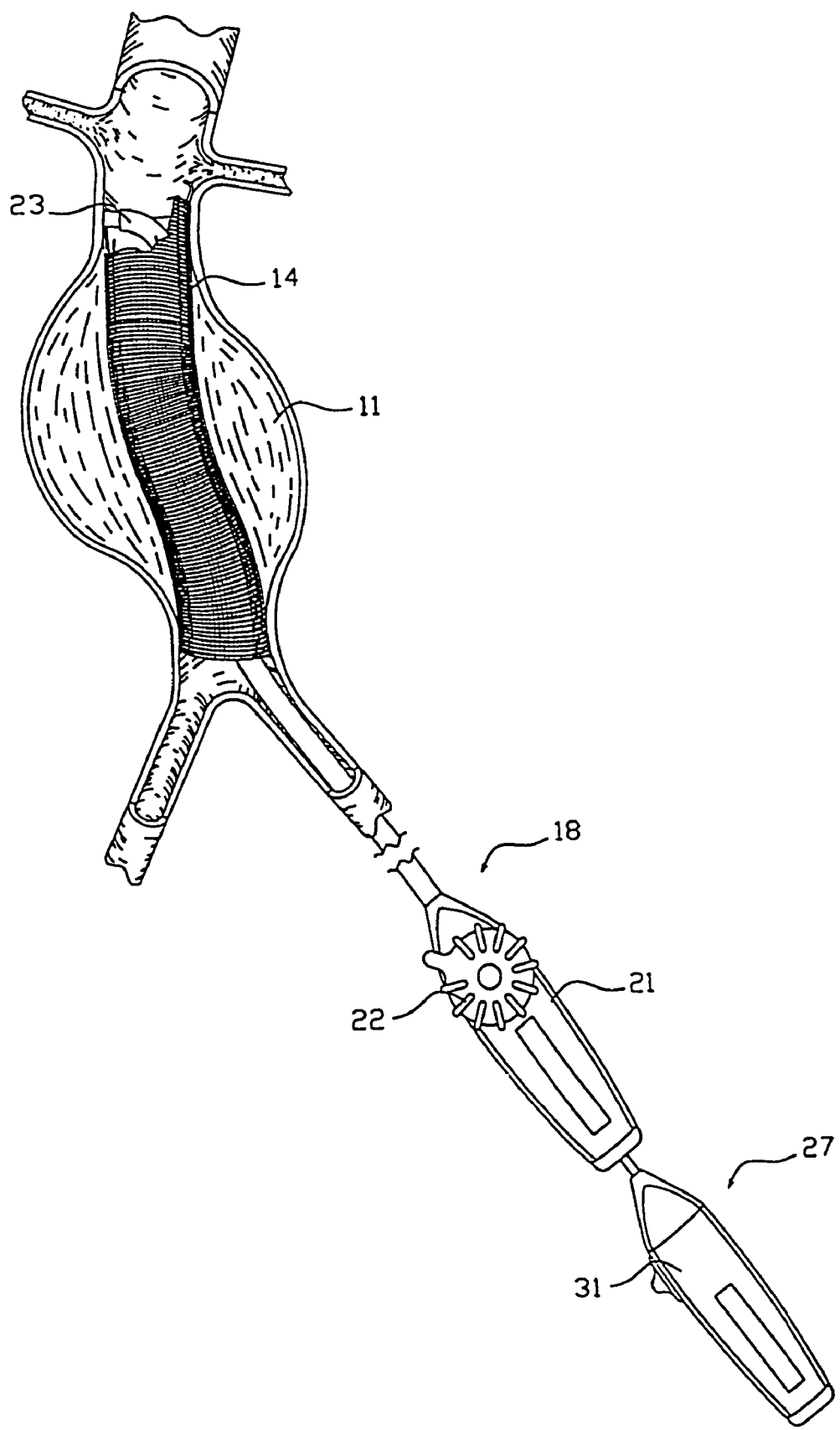
FIG. 15 is a perspective view of the fastener applier of FIG. 14 being positioned within directing device of FIG. 6.

The operator actuates the control unit 31 by contacting a control switch 110 (see FIGS. 14 and 14B). This action causes the helical fastener 28 to be rotated off the carrier 102 and through the prosthesis 14 and into the vessel wall 34. The motor control unit 31 desirably rotates the drive cable 30 a specific number of revolutions with each activation command. This can be accomplished by incorporating a mechanical or electrical counter.

With the deployment of a fastener 28, the fastener applier component 27 is retrieved through the directing component 18, and another fastener 28 is loaded into the carrier 102. The directing component 18 is repositioned, and the applier component 27 is advanced again through the directing component 18 and into contact with the prosthesis 14. The operator again actuates the control unit 31 by contacting the control switch 110 to deploy another fastener 28. This process is repeated at both proximal and/or distal ends of the prosthesis 14 until the prosthesis 14 is suitably attached and sealed to the vessel wall 34. It is contemplated that from about two to about twelve fasteners 28 may be applied at each end of the prosthesis 14 to affect anchorage. The fasteners 28 can be applied in a single circumferentially space-apart row, or may be applied in more than one row with individual fasteners being axially aligned or circumferentially staggered.

Figure 22:
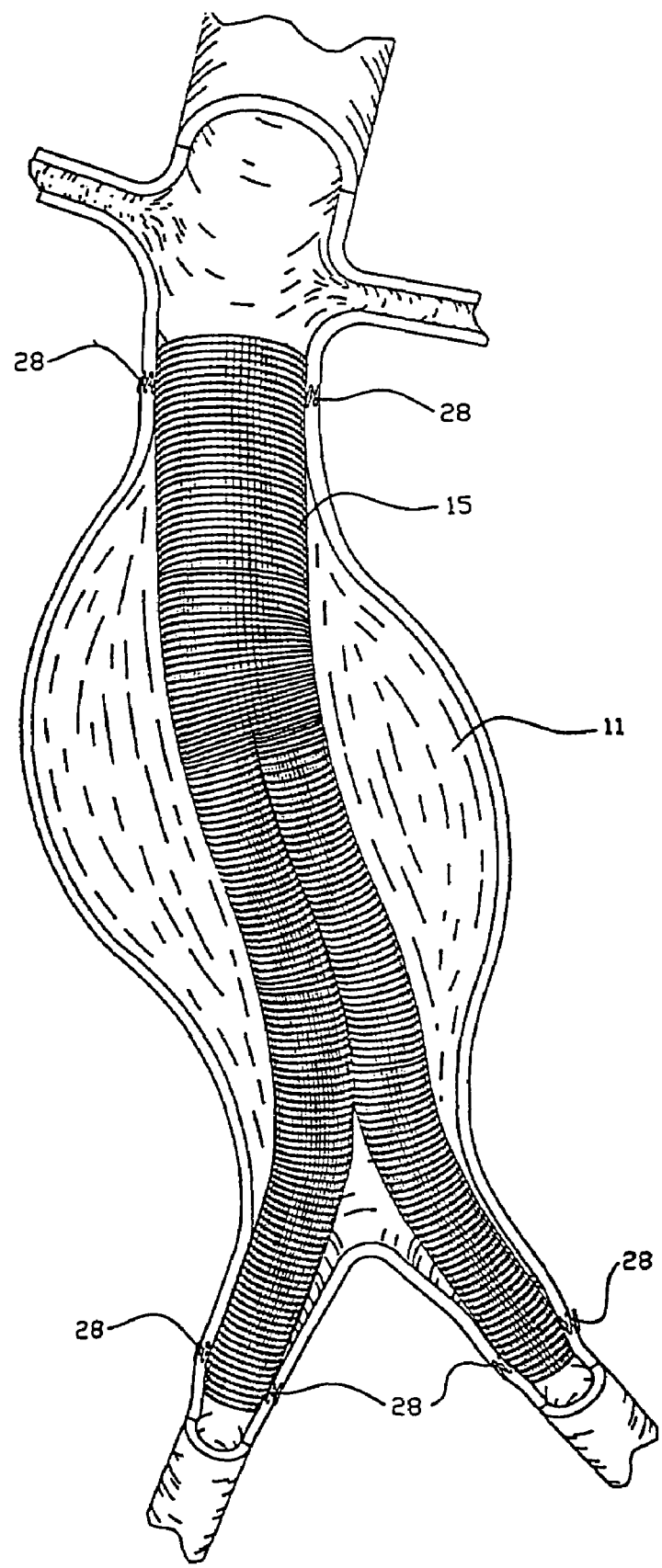
FIG. 22 is a perspective view of the graft of FIG. 4 completely attached to the vessel.

FIG. 22 illustrates a perspective view of a graft prosthesis attached to the vessel wall both proximally and distally. It is contemplated that the present invention can be used for graft attachment of both straight and bifurcated grafts within the aorta and other branch vessels.

Figure 25A:
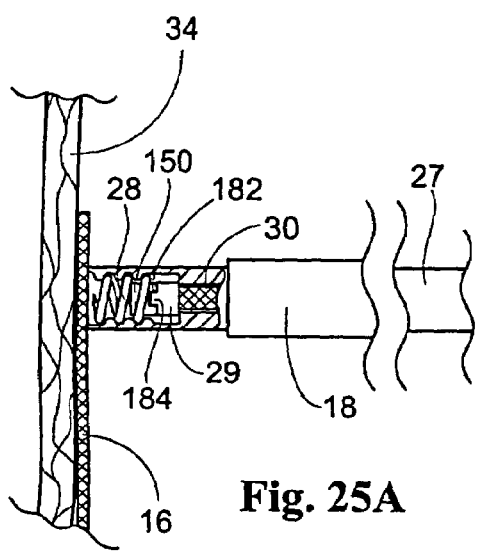
FIGS. 25A and 25B are enlarged views of the distal end of a fastener applier showing the details of an alternative embodiment of the fastener drive mechanism.
Figure 25B:
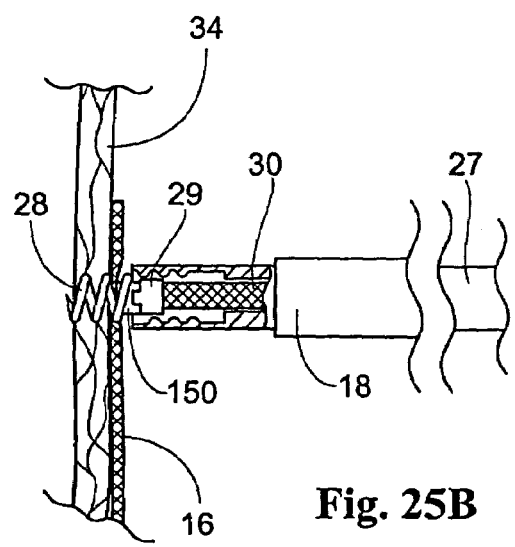
Figure 27:
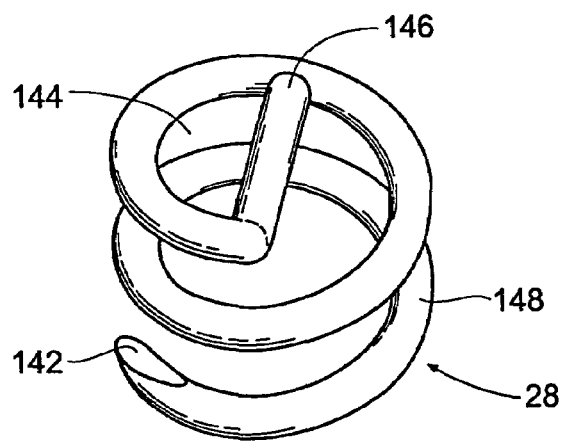
FIG. 27 is a perspective view of a helical fastener that can be used in association with the fastener applier shown in FIGS. 14, 23, and 24.
Figure 28A:
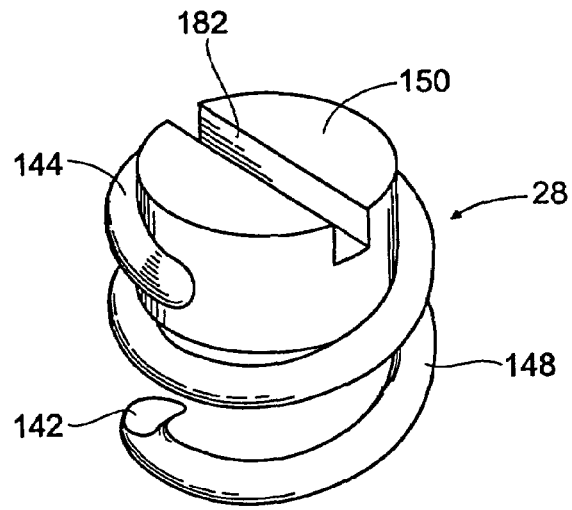
FIG. 28A is a perspective view of a helical fastener that can be used in association with the fastener applier shown in FIGS. 25A and 25B.

An alternative embodiment of the drive mechanism 100 is shown in FIGS. 25A and 25B. In this embodiment, the driver 29 is coupled to a carrier 150, which forms a part of the helical fastener 28 itself, as also shown in FIG. 28A. As shown in FIG. 28A, the helical fastener 28 is, like the fastener shown in FIG. 27, an open coil 148 with a sharpened leading tip 142. The proximal end 144 of the fastener 28 includes the carrier 150.

The carrier 150 includes a slot 182. The slot 182 engages a drive flange 184 on the driver 29 (see FIG. 25A) to impart rotation of the driver 29 to rotation of the helical fastener 28 during the implantation process. Like the L-shaped leg of the fastener shown in FIG. 27, the carrier 150 also serves as a stop to prevent the helical fastener from penetrating too far into the tissue.

The coupling engagement between the carrier 150 and the driver 29 could be accomplished in various ways, e.g., by separate graspers or grippers, a magnetic couple, or any other suitable mechanical connecting means. In the illustrated embodiment, the driver 29 is made of a magnetized material, and the carrier 150 is made from a material that is magnetically attracted toward the magnetized material. Of course, a reverse arrangement of magnetized and magnetically attracted materials could be used.

In this arrangement, the motor coupling 132 between the drive cable 30 and the motor 106 accommodates axial displacement of the motor cable 30 (left and right in FIGS. 25A and 25B) without interrupting the drive connection with the motor 106. With the distal tip of the applier device 27 in contact with the prosthesis 14 (see FIG. 25A), the operator actuates the control unit 31 by contacting a control switch 110. The control unit 31 commands the motor 106 to rotate the drive cable 30 to impart rotation to the driver 29 and the magnetically attached helical fastener 28. This action causes the magnetically attached helical fastener 28 to be rotated into prosthesis 14 and the vessel wall 34 (see FIG. 25B). Due to the magnetic coupling, as the fastener 28 is deployed to the left in FIG. 25B, the driver 29 moves in tandem with carrier 150

(also to the left in FIG. 25B). Due to the magnetic coupling between the carrier 150 and the driver 29, the operator must exert a deliberate separation force to decouple the carrier 150 (and, with it, the fastener 28) from the driver 29. This arrangement prevents inadvertent release of a fastener 28.

As before described, with the deployment of a fastener 28, the applier component 27 is retrieved through the directing device 18, and another fastener 28 is magnetically coupled to the driver 29. The directing component 18 is repositioned, and the applier component 27 is advanced again through the directing component 18 and into contact with the prosthesis 14. The operator again actuates the control unit 31 by contacting a control switch 110 to deploy another fastener 28. This process is repeated at both proximal and/or distal ends of the prosthesis 14 until the prosthesis 14 is suitably attached and sealed to the vessel wall 34.

As indicated in the above description, the outer diameter of the applier component 27 is desirably sized and configured to pass through the lumen of the directing component 18, which can take the form of a suitable steerable guide catheter, to direct the applier component 27 to the desired location. As also above described, the applier component 27 is desirably configured to implant one fastener 28 at a time (a so-called "single fire" approach). This is believed desirable, because it reduces the complexity of the design and accommodates access of the applier component 27 through tortuous anatomy. A fastener applier component 27 which carries a single fastener can have a lower profile and may be more effective and less traumatic than fastener appliers which carry multiple fasteners. Still, in alternative embodiments, the applier component 27 may, if desired, be configured to carry multiple fasteners. Moreover, the fastener applier 27 may simultaneously deploy multiple fasteners in the preferred circumferentially spaced-apart space pattern described above.

3. Force Resolution

Penetration and implantation of the fastener 28 into tissue using the applier component 27 requires the applier component 27 to exert an implantation force at or near the prosthesis 14 and vessel wall 34. In the illustrated embodiment, the applier component 27 comprises a driven member for implanting a helical fastener. However, the applier component 27 can comprise virtually any actuated member for exerting an implantation force using, e.g., ultrasonic, laser, or impact concepts.

Regardless of the particular way that the implantation force is generated, the implantation force of the applier component 27 is desirably resolved in some manner to provide positional stability and resist unintended movement of the applier component 27 relative to the implantation site. Stated differently, a resolution force is desirably applied to counteract and/or oppose the implantation force of the applier component 27. It is desirable to resolve some or all or a substantial portion of the implantation force within the vessel lumen (or other hollow body organ) itself, and preferably as close to the implantation site as possible.

The tubular body of the directing component 18 and/or the shaft of the fastener applier component 27 can be sized and configured to possess sufficient column strength to resolve some or all or at least a portion of the implantation force within the vessel lumen or hollow body organ. In addition, or alternatively, the directing component 18 and/or the fastener applier component 27 can include stabilization means 20 for applying a counteracting force at or near the driven member of the fastener applier component 27 that implants the fastener.

Figure 10:
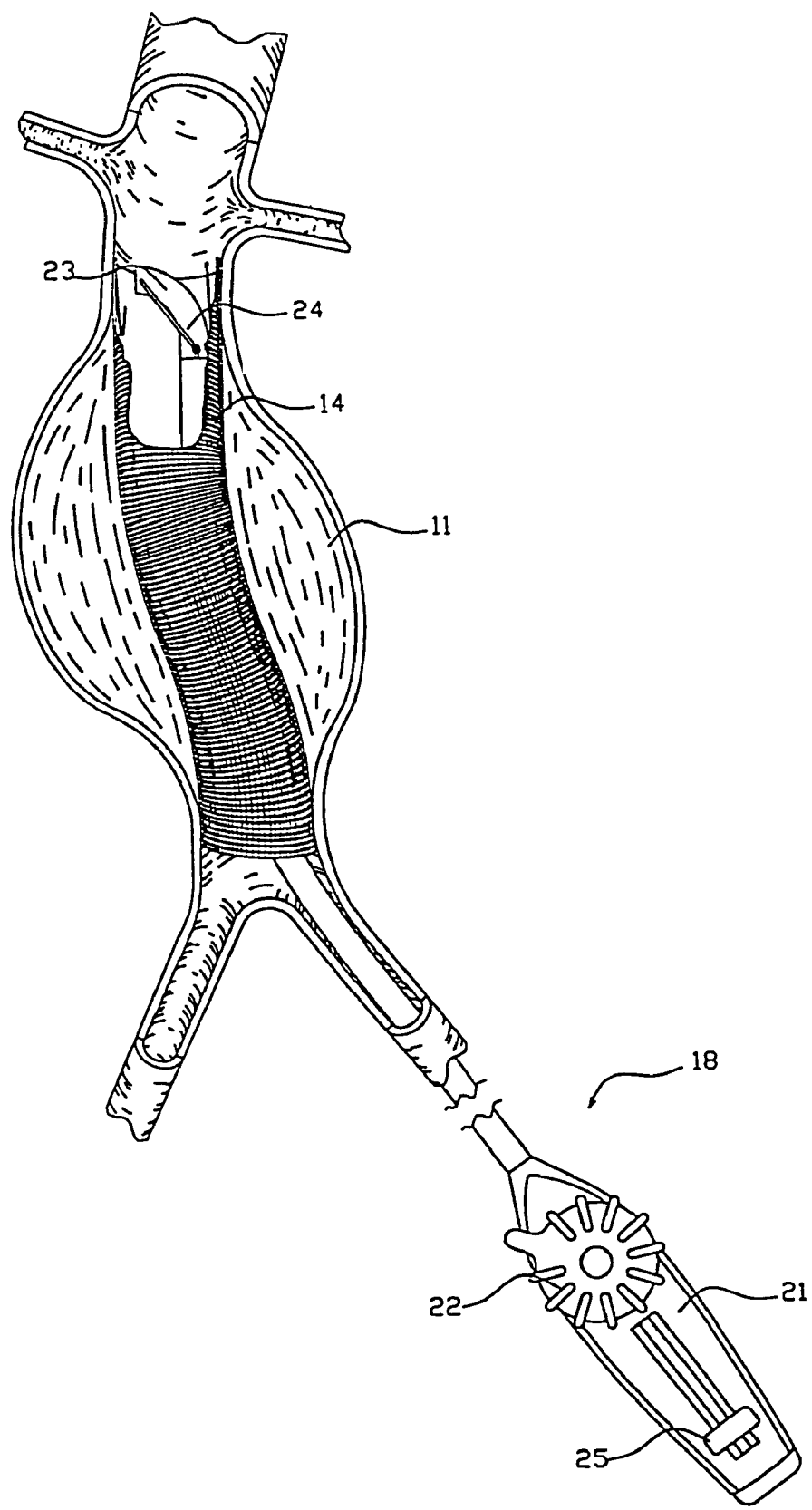
FIG. 10 is a perspective view of an alternative embodiment of the stabilization device of FIG. 8.
Figure 11:
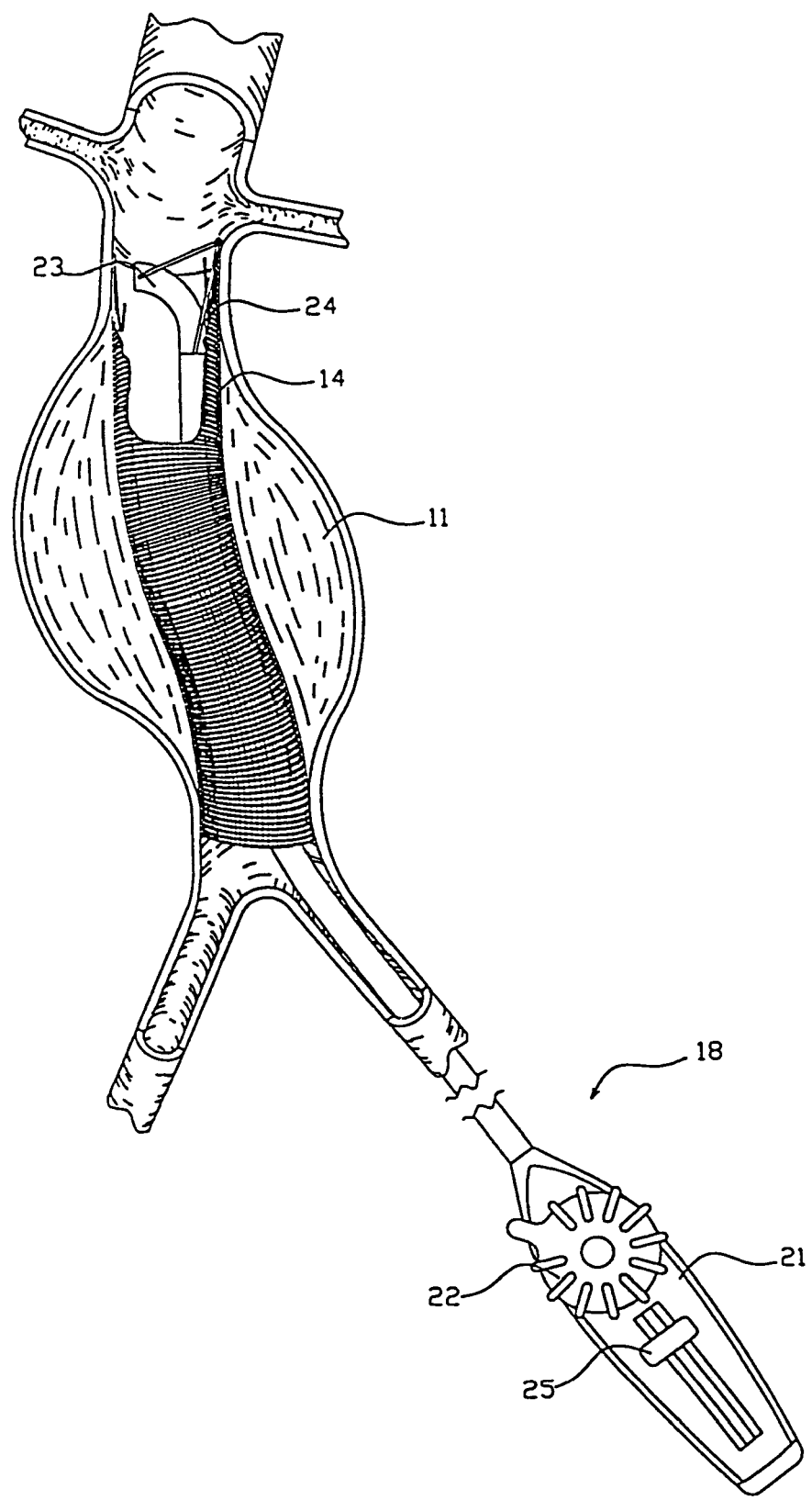
FIG. 11 is a perspective view showing the activation of the alternative stabilization device of FIG. 10.
Figure 12:
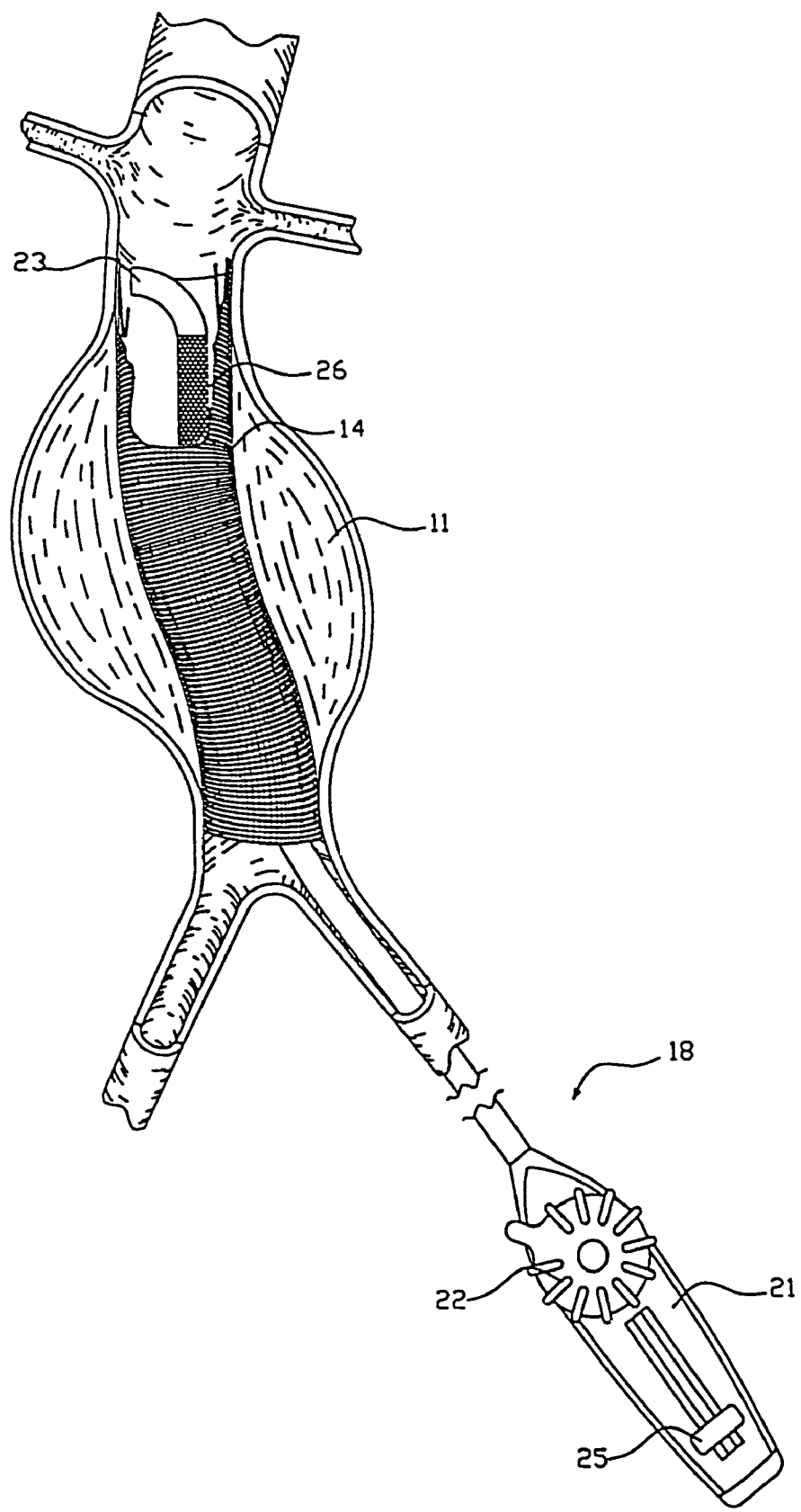
FIG. 12 is a perspective view showing another embodiment of the stabilization device of FIG. 8.
Figure 13:
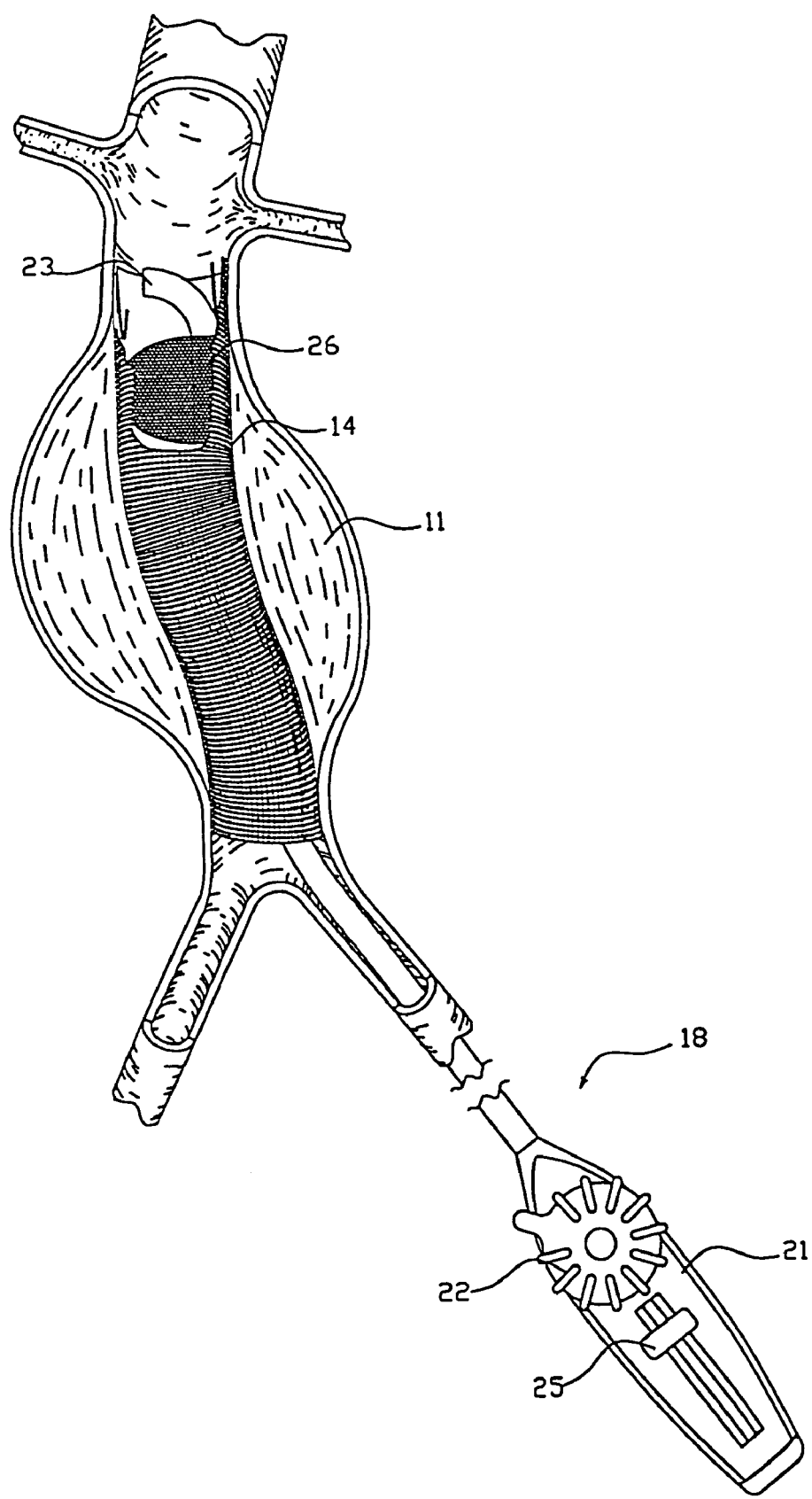
FIG. 13 is a perspective view showing activation of the stabilization device of FIG. 12.
Figure 43:
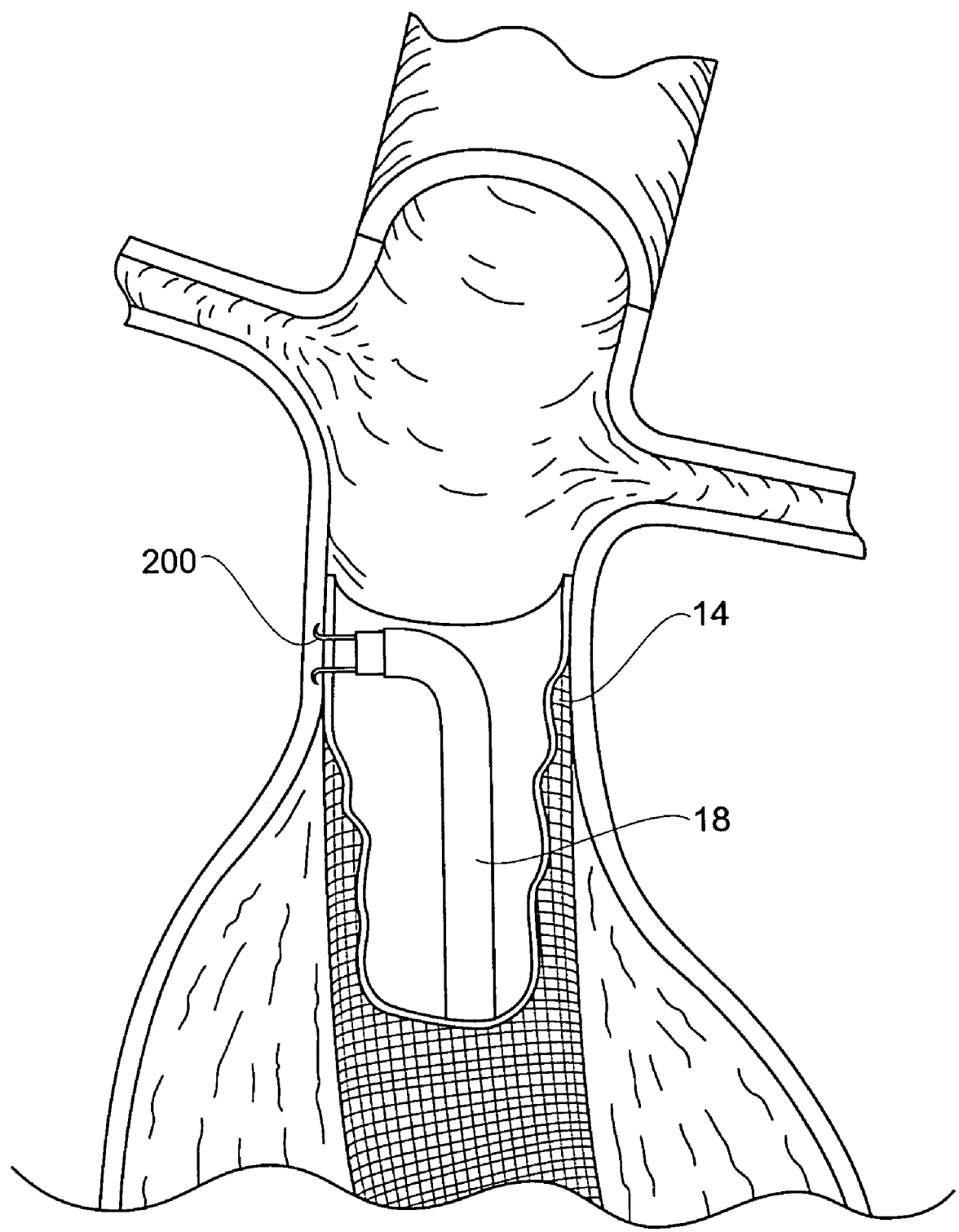
FIG. 43 is an elevation view of an alternative stabilization device, comprising tissue gripping elements.

The illustrated embodiments show various alternative embodiments for the stabilization means 20. As shown in FIGS. 8 and 9, the stabilization means 20 takes the form of a spring-loaded arm on the directing component 18 for contacting tissue. In this arrangement, the spring-loaded stabilizing means 20 is positioned for deployment when the obturator 19 and guidewire 12 are removed from the directing component 18 (see FIG. 8). In the alternative embodiment shown in FIGS. 10 and 11, the stabilization means 20 takes the form of a movable strut assembly 24 on the directing component 18, which contacts tissue. In this alternative arrangement, the movable strut assembly 24 can be activated, e.g., through a lever 25 on the control assembly (see FIG. 11). In both embodiments (FIGS. 7 and 10) the stabilizing device 20 is distal to the end of the directing component 18. In the alternative embodiment shown in FIG. 12, the stabilization means 20 takes the form of an expandable member 26 positioned adjacent the distal tip of the directing component 18. In this alternative arrangement (see FIG. 13), the expandable member 26 can be activated, e.g., through a lever 25 on the control assembly 21. However it also contemplated that this type of stabilizing means 20 could also be inflatable. In another alternative embodiment (see FIG. 43), the stabilization means 20 includes means 200 carried by the directing component 18 and/or the fastener applier component 27 for grasping and/or anchor to the wall of the hollow body organ, vessel or prosthesis prior to implanting a fastener. The grasping or anchoring means 200 can include penetrating needles and/or hooks or barbs that are deployed by a control assembly or the like prior to implantation of a fastener.

In all embodiments the stabilizing means 20 could be use to stabilize the directing component 18 either concentrically or eccentrically within the vessel.

Of course, any of these alternative forms of the stabilization means 20 can be associated with the fastener applier 27 in the same fashion they are shown to be associated with the directing component 18, or take some other form of a stabilization mechanism having the equivalent function. In yet another embodiment, the stabilization means 20 can take the form of a separate stabilization device used in cooperation with the directing component 18 and/or the fastener applier component 27. In this arrangement, the separate stabilization device could incorporate any of the alternative forms of the stabilizing devices described above, or some other form of stabilization mechanism.

Figure 44B:
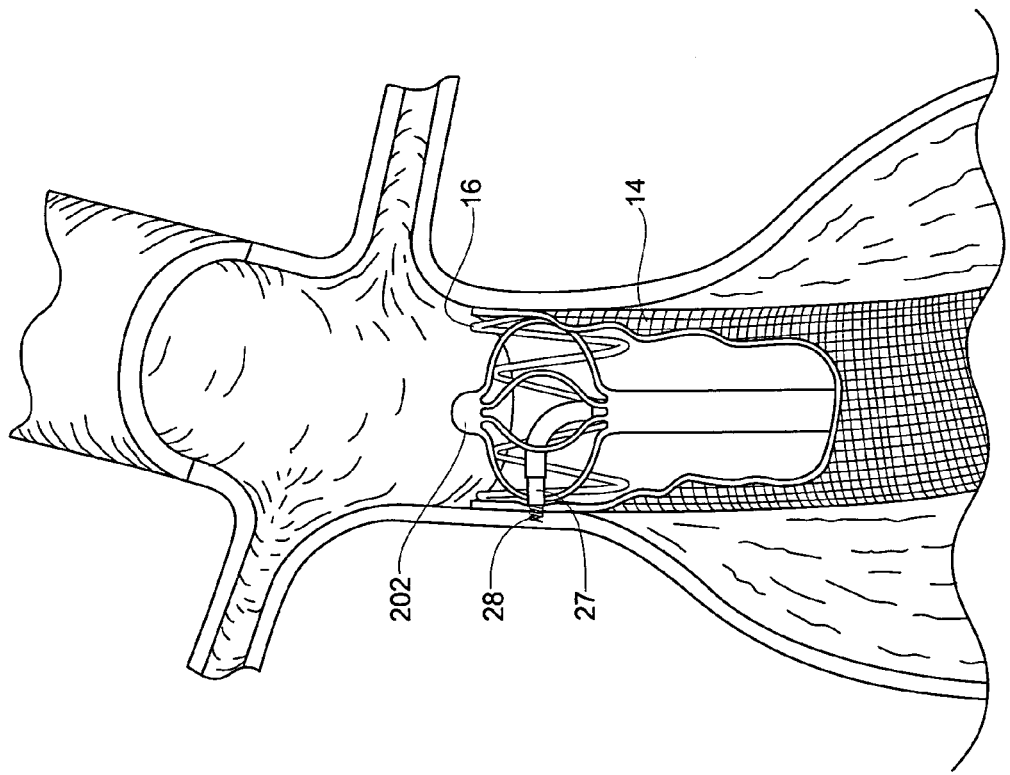
FIGS. 44A and 44B are elevation views of a fastener applier that carries an expandable basket-like structure that serves as a stabilization device, FIG. 44A showing the basket-like structure in a generally collapsed condition for intravascular deployment and FIG. 44B showing the basket-like structure in an expanded condition against a vessel wall and graft for deployment of a fastener.

For example (see FIGS. 44A and 44B), the fastener applier 27 can carry about its distal end an expandable basket 202 or basket-like structure. The basket structure 202 surrounds the fastener drive mechanism 100, which has been previously described. The basket structure 202 is operable between a low profile, generally collapsed condition (shown in FIG. 44A) and an expanded profile condition (shown in FIG. 44B) about the fastener drive mechanism 100.

Figure 44A:
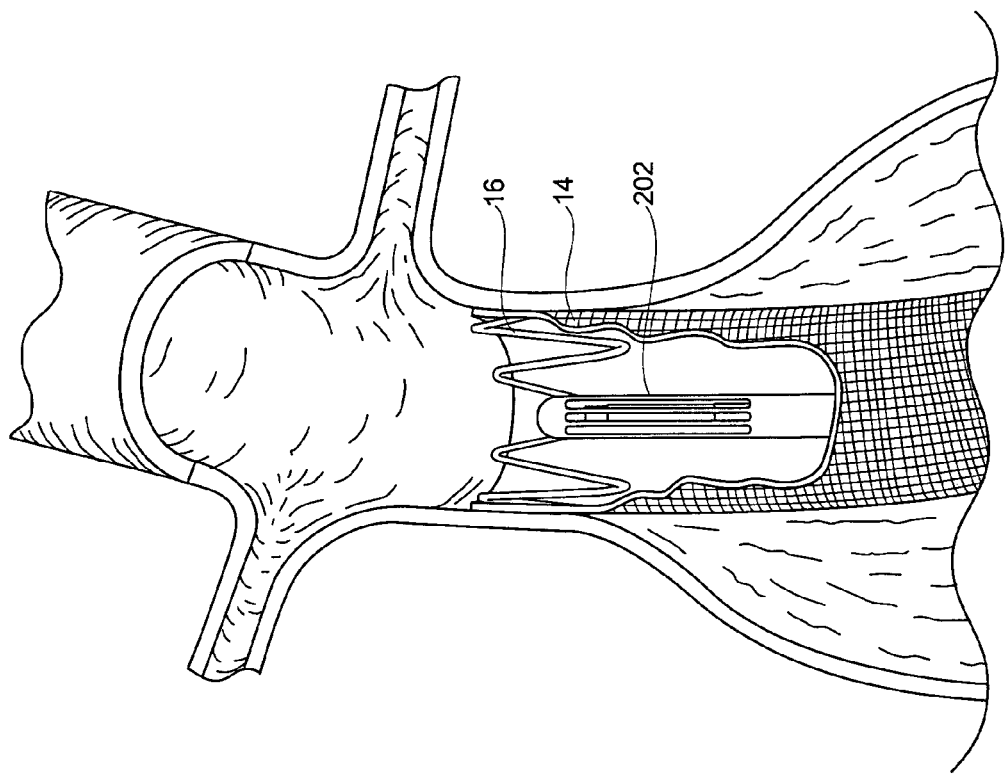

In the generally collapsed condition, the fastener applier 27 can be deployed through a vessel into proximity to a graft 14. FIG. 44A shows the graft 14 to include a self-expanding scaffold 16. When in the generally collapsed condition, the fastener applier 27 can be deployed in its low profile state through the vasculature to the targeted graft site either by itself, or through an associated directing component 18 or suitable guide sheath, which can steerable or non-steerable.

When situated at the graft site (see FIG. 44B), the basket structure 202 can be expanded (e.g., by a suitable push-pull control mechanism) into contact with the graft 14. The fastener applier 27 can be maneuvered within the expanded basket structure 202 into contact with the graft 14 and operated to deploy a fastener 28, as previously described. The basket structure 202 serves to resolve at least some of the implantation force to provide positional stability and resist unintended movement of the fastener applier 27.

Figure 45:
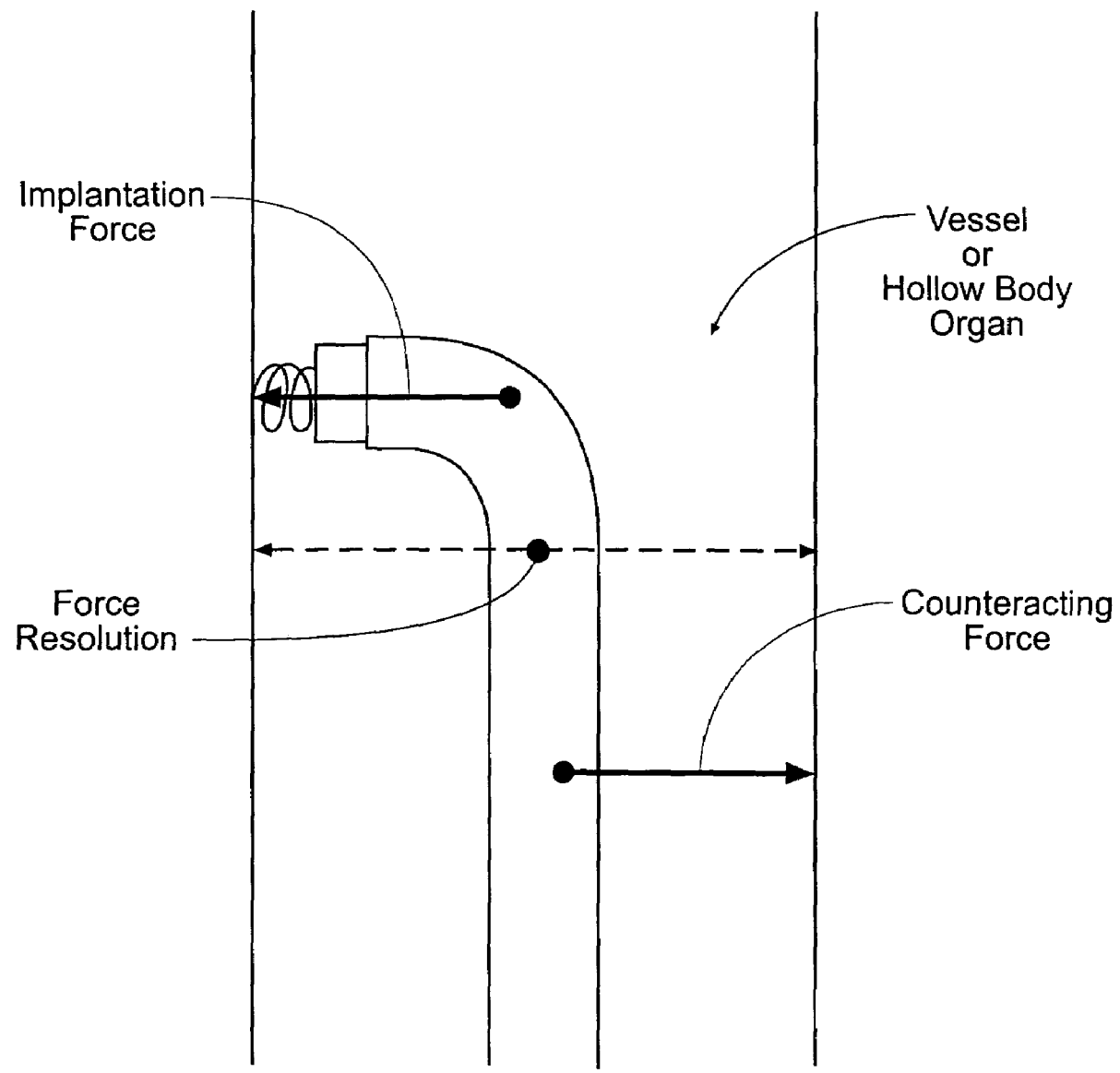
FIG. 45 shows, in diagrammatic fashion, the resolution of an implantation force with a counteracting force within a vessel or hollow body organ.

In all these alternative embodiments, the stabilization means 20 functions to apply a substantially equal and opposite counteracting resolution force within a vessel (see FIG. 45) to a location on the vessel wall, desirably generally opposite to the implantation site. As also just described, the column strength of the associated directing component 18 and/or fastener applier 27 can also serve in conjunction with the stabilization means 20 to resolve the intraluminal implantation force at the implantation site.

The force resolving function that the guiding component 18 and/or the fastener applier component 27 provide serves to counteract or oppose or otherwise resolve the tissue penetration and implantation force of the applier component 27. The force resolving function thereby also resists movement of the applier component 27 relative to the implantation site, thereby making possible a stable and dependable intraluminal (or intra organ) fastening platform.

4. Prosthesis/Tissue Contact Sensing

The fastener applier component 27 desirably incorporates a function that prevents actuation of the motor 106 until the tip of the applier component 27 is in a desired degree of contact with the prosthesis or tissue surface. This prevents inadvertent discharge of a fastener 28 and/or separation of the fastener 28. This function can be implemented, e.g., using a contact or force sensor, which is either mechanical or electrical in design.

When the fastener applier component 27 is of the type shown in FIGS. 14A, 14B, and 14C (see FIGS. 23 and 24), the contact or force sensing function can, e.g., utilize the distal tip 120 of the carrier 102 to transmit a contact force. This force can be transmitted to a force or contact sensing switch 122 located, e.g., within the fastener applier handle 108. In this arrangement, the switch 122 can be part of the electrical circuit between the actuator switch 110 and the control unit 31.

In the illustrated embodiment, the switch 122 includes a stationary switch element 128 (coupled to the interior of the handle 108) and a movable switch element 130 (carried by the drive cable 31). In this arrangement, the motor coupling 132 between the drive cable 30 and the motor 106 accommodates axial displacement of the motor cable 30 (left and right in FIGS. 23 and 24) without interrupting the drive connection with the motor 106. The drive cable 30 is coupled by a bearing 134 to the movable switch element 130, so that the switch element 130 moves in response to movement of the drive cable 30. The stationary switch element 128 is not coupled to the movable drive cable 30, which slidably passes through the switch element 130.

Due to this arrangement, axial displacement of the drive cable 30 moves the switch element 130 relative to the switch element 128. More particularly, displacement of the drive cable 30 to the left in FIG. 23 moves the switch element 130 to the left, away from the switch element 128. Conversely, displacement of the drive cable 30 to the right in FIG. 23 moves the switch element 130 to the right, toward the switch element 128.

A spring 126 normally biases the switch elements 128 and 130 apart, comprising an electrically opened condition. In this condition, operation of the actuating switch 110 does not serve to actuate the control unit 31, as the electrically open switch 122 interrupts conveyance of the actuation signal to the motor control unit 31. When the switch elements 128 and 130 are in the electrically opened condition, the drive cable 30 is displaced to the left to position the carrier tip 120 beyond the distal tip 124 of the fastener applier 27. The carrier tip 120 therefore makes contact with the prosthesis 14 or tissue in advance of the applier tip 124.

Figure 23:
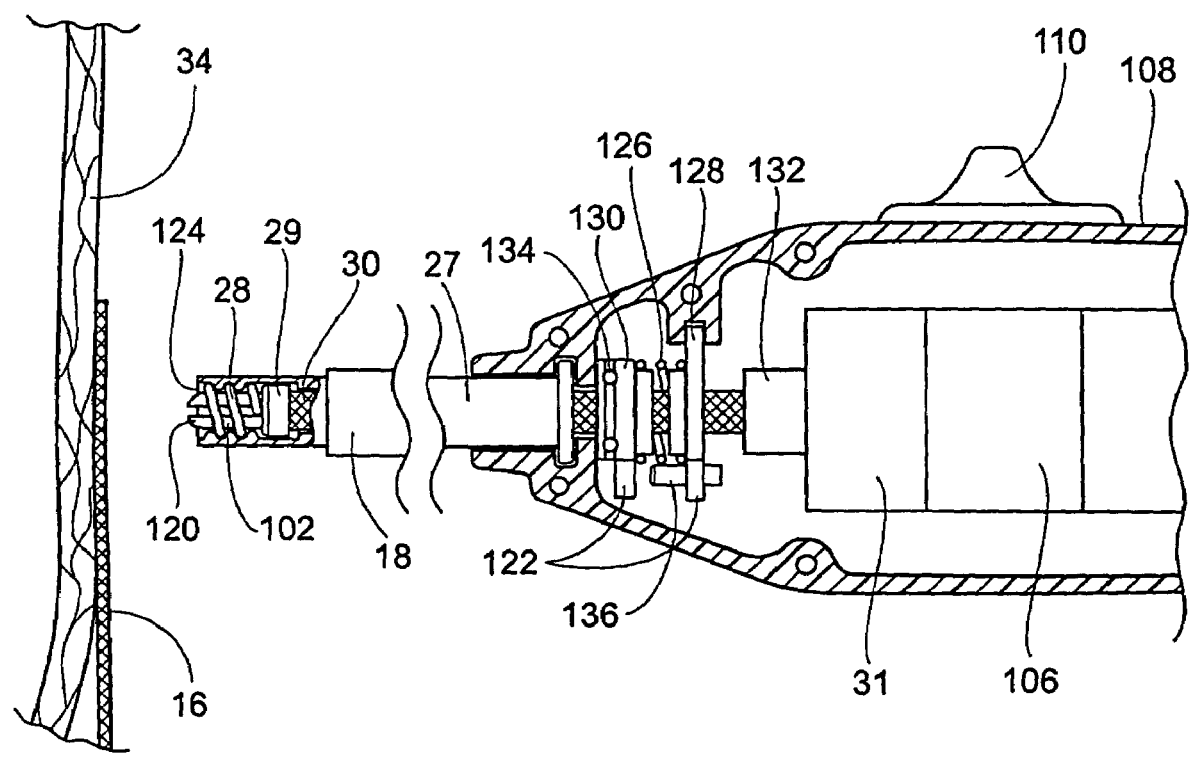
FIG. 23 is an enlarged section view of the drive mechanism of the fastener applier shown in FIG. 14, showing a contact/force sensing assembly that disables the applier in the absence of desired contact between the fastener and a targeted tissue region.

When the carrier tip 120 contacts the surface of the prosthesis or tissue with sufficient force to compress the spring 126, the drive cable 30 is displaced against the biasing force of the spring to the right in FIG. 23.

Figure 24:
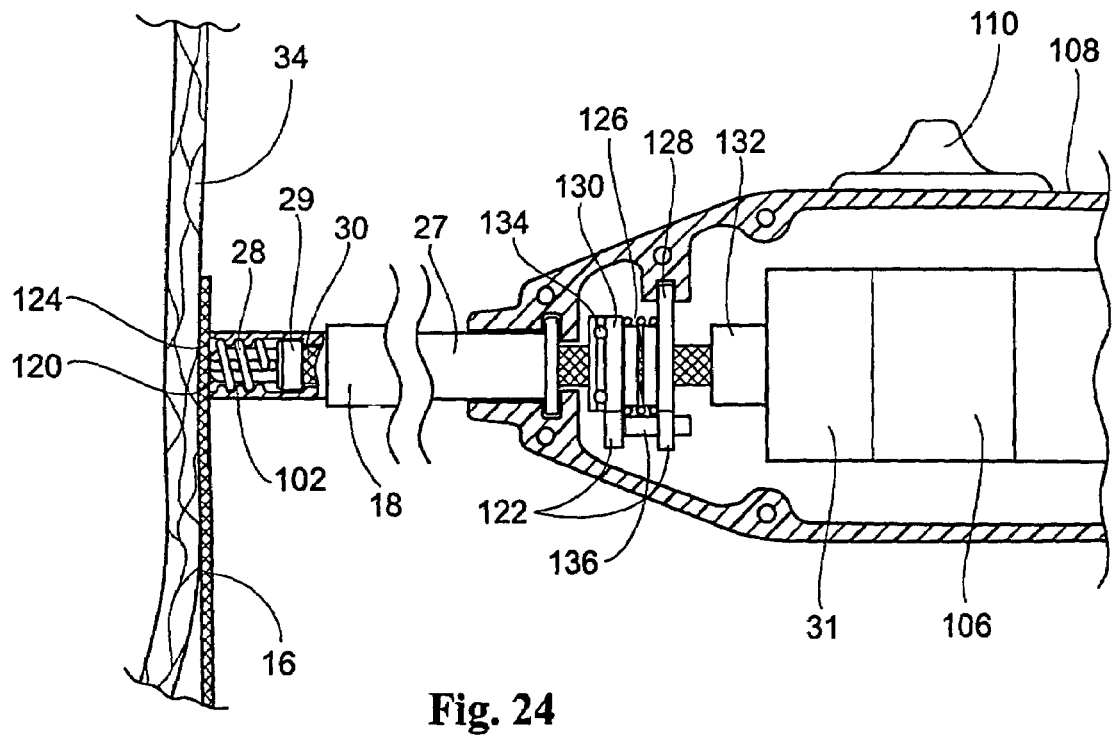
FIG. 24 is an enlarged section view of the drive mechanism of the fastener applier shown in FIG. 14, showing the contact/force sensing assembly enabling use of the applier in response to desired contact between the fastener and the targeted tissue region.

This moves the switch element 130 to the right. Ultimately, contact between the switch elements 128 and 130 will occur, as shown in FIG. 24. The contact establishes an electrically closed condition. In this condition, operation of the actuating switch 110 serves to actuate the control unit 31. As shown in FIGS. 23 and 24, a contact screw 136 can be provided to adjust the amount of displacement required to close the switch elements 128 and 130.

Upon removal of contact force, or in the absence of sufficient contact force, the spring 126 urges the switch elements 128 and 130 toward the electrically opened condition. The distal tip of the carrier 102 is located distally beyond the distal tip of the applier 27.

It should be appreciated that the translation of movement of the carrier tip 120 to the switch 122 need not occur along the entire length of the drive cable 30. For example, the switch 122 can be located in a translation space between the carrier 102 and the driver 29. In this arrangement, the driver 29, coupled to the drive cable 30 need not accommodate axial displacement. Instead, relative movement of the carrier 102 toward the driver 29 in response to contact with the prosthesis 14 will mechanically couple the carrier 10 with the driver 29 (e.g., through a slot and flange connection similar to that shown in FIGS. 25A and 25B), while also closing the switch 122 to energize the circuit between the actuator switch 110 and the motor control unit 31.

Figure 28B:
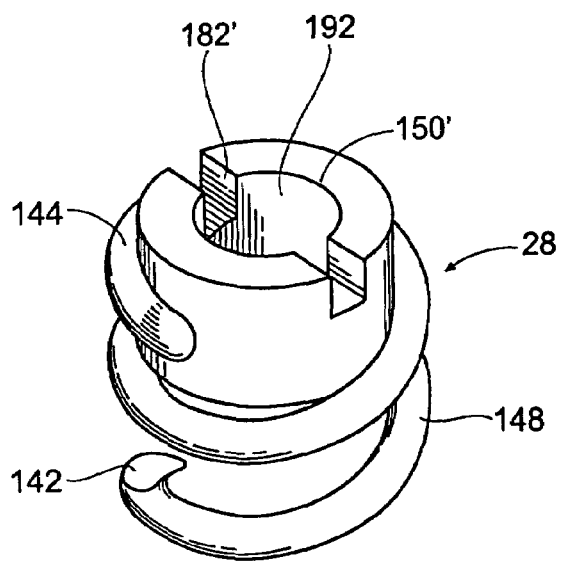
FIG. 28B is perspective view of a helical fastener that can be used in association with the fastener applier shown in FIGS. 26A to 26C.

When the fastener applier component 27 is of the type shown in FIGS. 25A and 25B (see FIGS. 26A, 26B, and 26C), the contact or force sensing function can, e.g., utilize a force sensing rod 190 that slidably passes through a central passage 192 in the carrier 150' (the carrier 150' is shown in FIG. 28B), the driver 29 and the drive cable 30. The rod 190 is coupled to the movable switch element 130. In this embodiment, the switch element 130 translates left and right over the drive cable 30, which rotates on a bearing 134 within the switch element 130.

As in the preceding embodiment, the spring 126 normally biases the switch elements 128 and 130 apart, comprising an electrically opened condition. When the switch elements 128 and 130 are in the electrically opened condition, the force sensing rod 190 is displaced to the left beyond the distal tip 124 of the fastener applier component 27. The force sensing rod 190 therefore makes contact with the prosthesis 14 or scaffold structure 16 in advance of the applier tip 124.

Figure 26A:
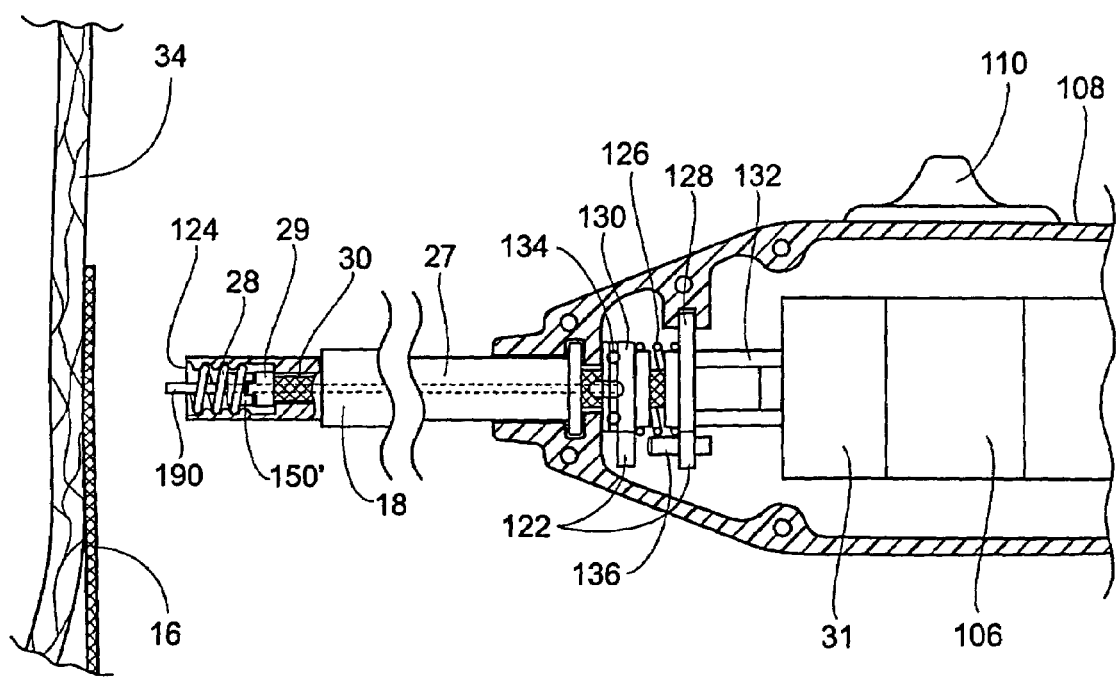
FIG. 26A is an enlarged section view of the drive mechanism of the fastener applier shown in FIGS. 25A and 25B showing a contact/force sensing assembly that disables the applier in the absence of desired contact between the fastener and a targeted tissue region.
Figure 26B:
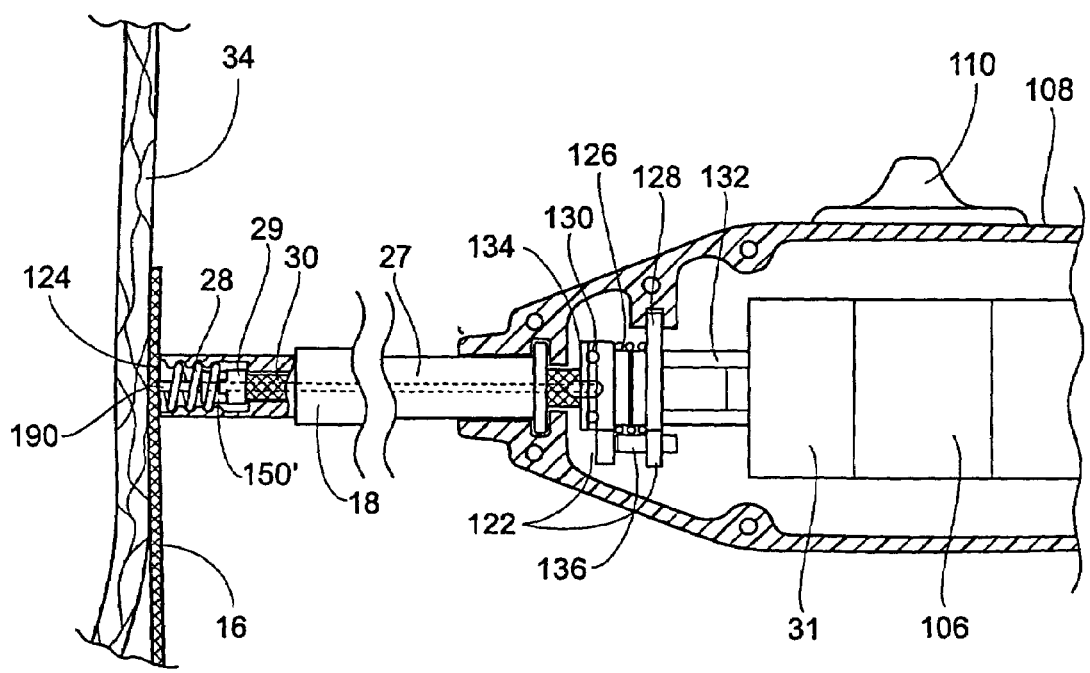
FIGS. 26B and 26C are enlarged section views of the drive mechanism of the fastener applier shown in FIGS. 25A and 25B, showing the contact/force sensing assembly enabling use of the applier in response to desired contact between the fastener and the targeted tissue region.

When the rod 190 contacts the surface of the prosthesis or scaffold structure with sufficient force to compress the spring 126, the rod 190 is displaced against the biasing force of the spring 126 to the right in FIG. 26A. This moves the switch element 130 to the right. Ultimately, contact between the switch elements 128 and 130 will occur, as shown in FIG. 26B. The contact establishes an electrically closed condition. In this condition, operation of the actuating switch 110 serves to actuate the control unit 31. This action causes the helical fastener 28 to be rotated into the scaffold structure 16 and into the vessel wall 34 (see FIG. 26C). Due to the magnetic coupling between the driver 29 and carrier 150', the driver 29 is moved in tandem with attached carrier 150' to the left in FIG. 26B, as the fastener 28 is deployed. Also, due to the magnetic coupling between the carrier 150 and the driver 29, the operator must exert a separation force to decouple the carrier 150

(and, with it, the fastener 28) from the driver 29. As before described, this arrangement prevents inadvertent release of a fastener 28. A contact screw 136 can be provided to adjust the amount of displacement required to close the switch elements 128 and 130.

Upon removal of contact force, or in the absence of sufficient contact force, the spring 126 urges the switch elements 128 and 130 toward the electrically opened condition, moving the tip of the rod 190 out beyond the distal tip 124 of the applier 27.

The contact or force sensing arrangements just described can also generate an audible and/or visual output to the operator, to indicate that sufficient contact force between the applier device 27 and the prosthesis or tissue exists.

B. Angled Component Fastener Guide and Attachment Assembly

In another arrangement (see FIG. 29), the fastener attachment assembly comprises a unitary, angled fastener guide and applier component 160. In this arrangement, the component 160 includes a fastener drive mechanism 162 that places the carrier 164 holding the fastener 28 in a perpendicular or near perpendicular position with respect to the prosthesis or tissue. This configuration eliminates the need for a separate steerable guide component 18 for the fastener component 27, previously described.

Figure 29:
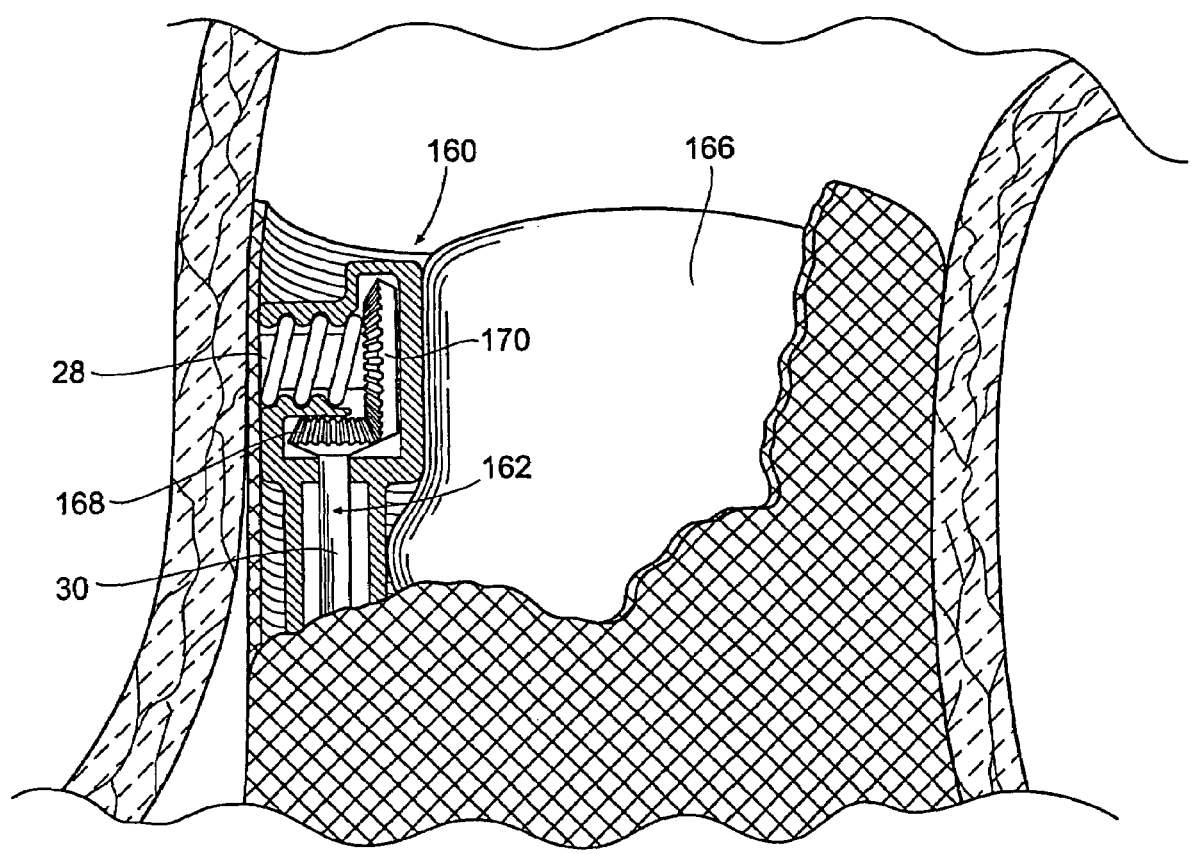
FIG. 29 is an enlarged side view, partially in section, of a fastener applier having an angled applicator end that can be used to deploy the helical fastener shown in FIG. 27 without use of a separate directing device.

The drive mechanism 162 can vary. In the illustrated embodiment (shown in FIG. 29), the mechanism 162 includes a beveled drive gear 168 coupled to the drive cable 30. The drive gear 168 operatively meshes with a transfer or pinion gear 170, which is coupled to the carrier 164. The axes of rotation of the drive gear 168 and pinion gear 170 are offset about ninety degrees, so that rotation of the drive cable 30 along the axis of the vessel is translated into rotation of the carrier 164 generally perpendicular to the wall of the vessel. The fastener guide and applier component 160 can be positioned and stabilized within the vessel in various ways, e.g., through the use external spring loaded strut or the like (as shown in association with the directing component 18 discussed above), or by use of an expandable member 166 (as FIG. 29 shows). The expansion member 166 can comprise either a balloon or mechanical expansion device. The expansion member 166 stabilizes the position of both the prosthesis and the fastener guide and applier component 160 within the vessel by resisting the force of blood until the prosthesis can be anchored.

Figure 30:
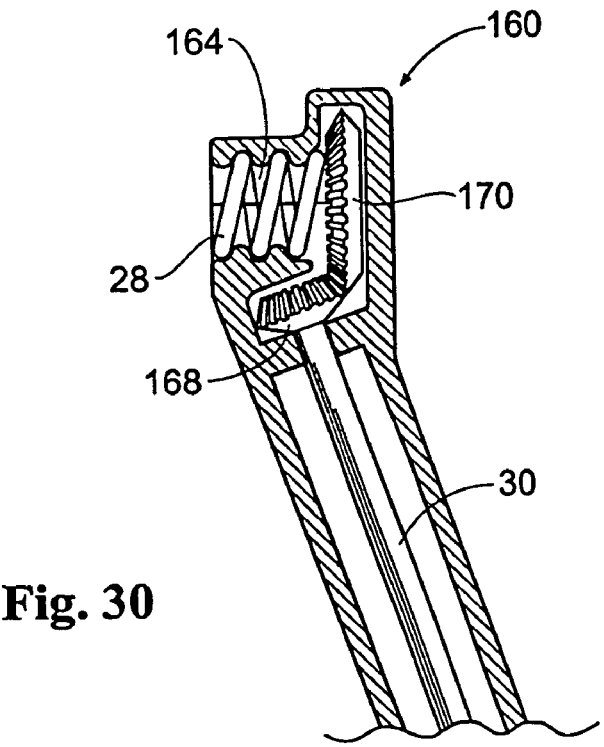
FIG. 30 is an enlarged side view, partially in section, of an alternative embodiment of an angled fastener applier that can be used to deploy the helical fastener shown in FIG. 27 without use of a separate directing device.
Figure 31:
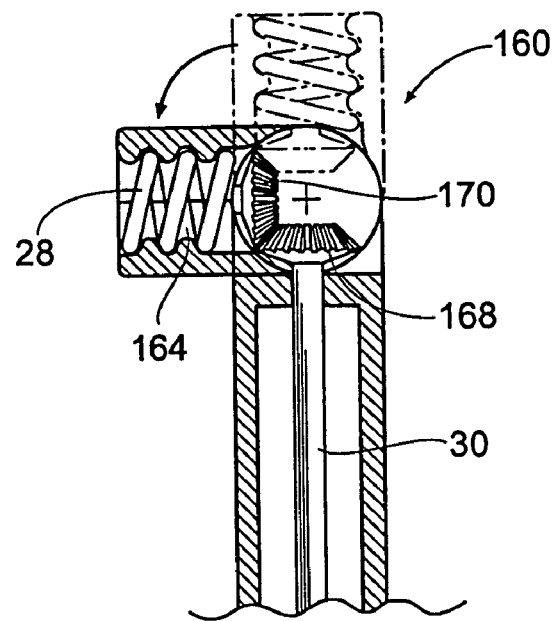
FIG. 31 is an enlarged side view, partially in section, of an alternative embodiment of an angled fastener applier that can be used to deploy the helical fastener shown in FIG. 27 without use of a separate directing device, the fastener applier having an articulating applicator end.

As FIG. 30 shows, the fastener guide and applier component 160 can, if desired, provide an angled deployment between the drive cable 30 and carrier 164 that is somewhat less than ninety-degrees, to aid in intraluminal manipulation of the carrier into perpendicular contact position against the wall of the vessel. As FIG. 31 shows, the fastener guide and applier component 160 can, if desired, be articulated between the drive cable 30 and carrier 164. In this arrangement, a remote control mechanism is desirable provided to move the carrier 164 from a first, generally straight position (shown in phantom lines in FIG. 31) for deployment to the targeted site, to a second, articulated position (shown in solid lines in FIG. 31) for alignment of the carrier 164 in contact against the vessel wall.

III. The Fasteners

As illustrated and described thus far, introduction of the fasteners 28 will typically be affected after the prosthesis 14 has been initially placed. That is, initial placement of the prosthesis 14 will be achieved by self-expansion or balloon expansion, after which the prosthesis 14 is secured or anchored in place by the introduction of a plurality of individual fasteners. The fasteners 28 may be placed only through the fabric of the prosthesis 14, i.e., avoiding the scaffold structure. Alternately, the fasteners 28 can be introduced into and through portions of the scaffold structure itself. The prosthesis 14 may include preformed receptacles, apertures, or grommets, which are specially configured to receive the fasteners. The fasteners 28 may be introduced both through the fabric and through the scaffold structure. The fasteners can be introduced singly, i.e., one at a time, in a circumferentially spaced-apart pattern over an interior wall of the prosthesis 14.

In the exemplary embodiment, the fasteners 28 are helical fasteners, so that they can be rotated and "screwed into" the prosthesis 14 and vessel wall. A desired configuration for the helical fastener 28 (see FIGS. 27, 28A, and 28B) is an open coil 148, much like a coil spring. This configuration allows the fastener 28 to capture a large area of tissue, which results in significantly greater holding force than conventional staples, without applying tissue compression, which can lead to tissue necrosis.

As FIGS. 27, 28A, and 28B show, the leading tip 142 of the helical fastener 28 is desirable sharp to allow it to penetrate thought the artery wall and/or calcified tissue. This distal tip 142 can be sharpened to cut a helical path through the tissue or it can be sharpened to a point to penetrate the tissue without cutting.

The proximal end 144 of the fastener serves two design functions. The first function is to engage the carrier 102 of the fastener applier 27, which rotates the helical fastener during the implantation process. The second function is to act as a stop to prevent the helical fastener from penetrating too far into the tissue.

In one embodiment (see FIG. 27), the proximal end 144 of the helical fastener 28 includes an L-shaped leg 146 of the coil 148 bisecting the fastener diameter. The leg 146 of the coil 148 comes completely across the diameter to prevent the fastener from being an open coil and to control the depth of penetration into the tissue. In addition, the leg 146 of the coil 148 can be attached to a previous coil to strengthen the entire structure and provide a more stable drive attachment point for the fastener applier. This attachment could be achieved via welding, adhesive or any other suitable means.

Alternatively (as shown in FIGS. 28A and 28B), the proximal end 144 of the fastener 28 could incorporate a separate cap or carrier 150 or 150' that serves the same function as the leg 146 of the coil 148 in FIG. 27. The carrier 150 or 150' could feature several methods to attach to the fastener applier drive mechanism 100. These include separate graspers or grippers, a magnetic couple (as previously described), or any other suitable mechanical connecting means. In FIGS. 28A and 28B, the carrier 150 and 150' includes a slot 180 and 182' to mate with a drive flange (as previously described). As also previously described, a magnetic coupling is implemented between the carrier 150 and 150' and the corresponding drive member, to prevent inadvertent separation during use.

Figure 26C:
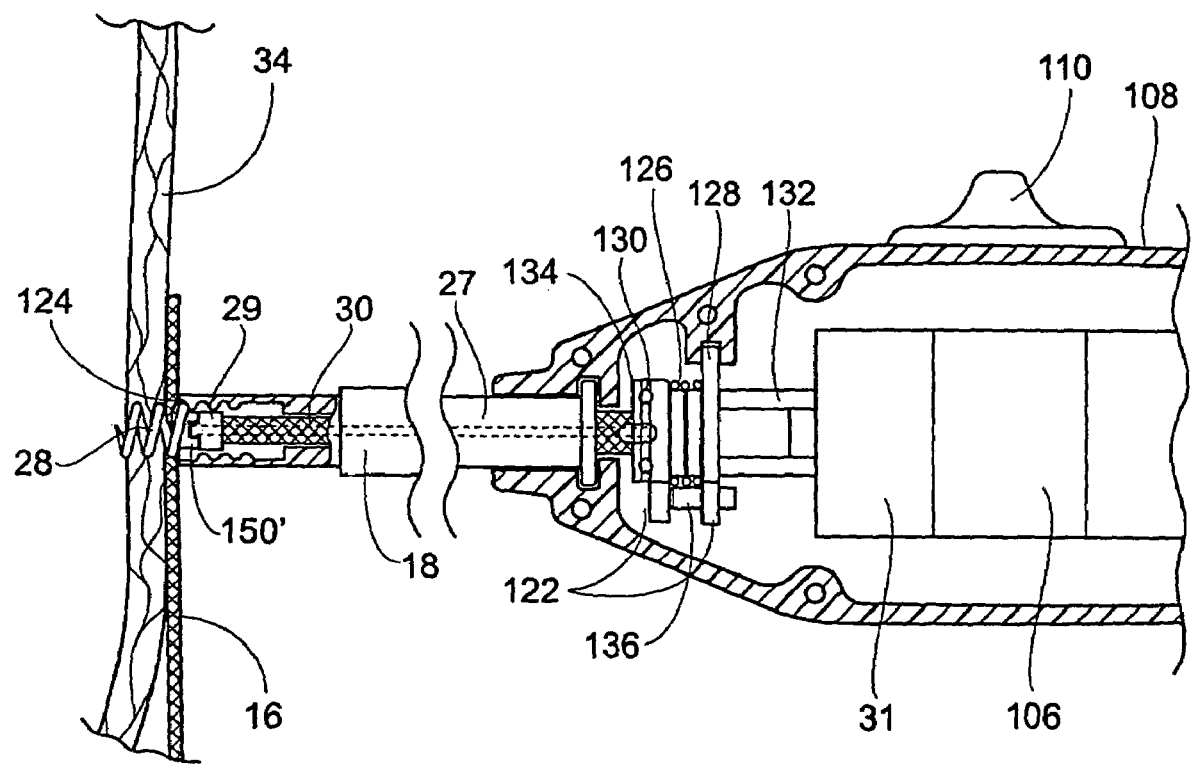

In FIG. 28B, the carrier 150' also includes a passage 152 for holding the contact/force sensing rod 190 shown in FIGS. 26A, 26B, and 26C.

The fasteners 28 shown in FIGS. 27, 28A, and 28B can be made from stainless steel or other types of implantable metal, however it is also envisioned that the fasteners in the above descriptions could be made from implantable polymers or from a biodegradable polymer or combinations of all materials thereof. Desirably, a fastener 28 will have between 2 and 10 turns and will be between 1 mm and 10 mm long. The space between the individual coils will be between 0.25 mm and 3 mm. The diameter of the fastener 28 will be between 1 mm and 6 mm.

IV. Prosthesis with Integrated Fastener Assembly

Figure 32:
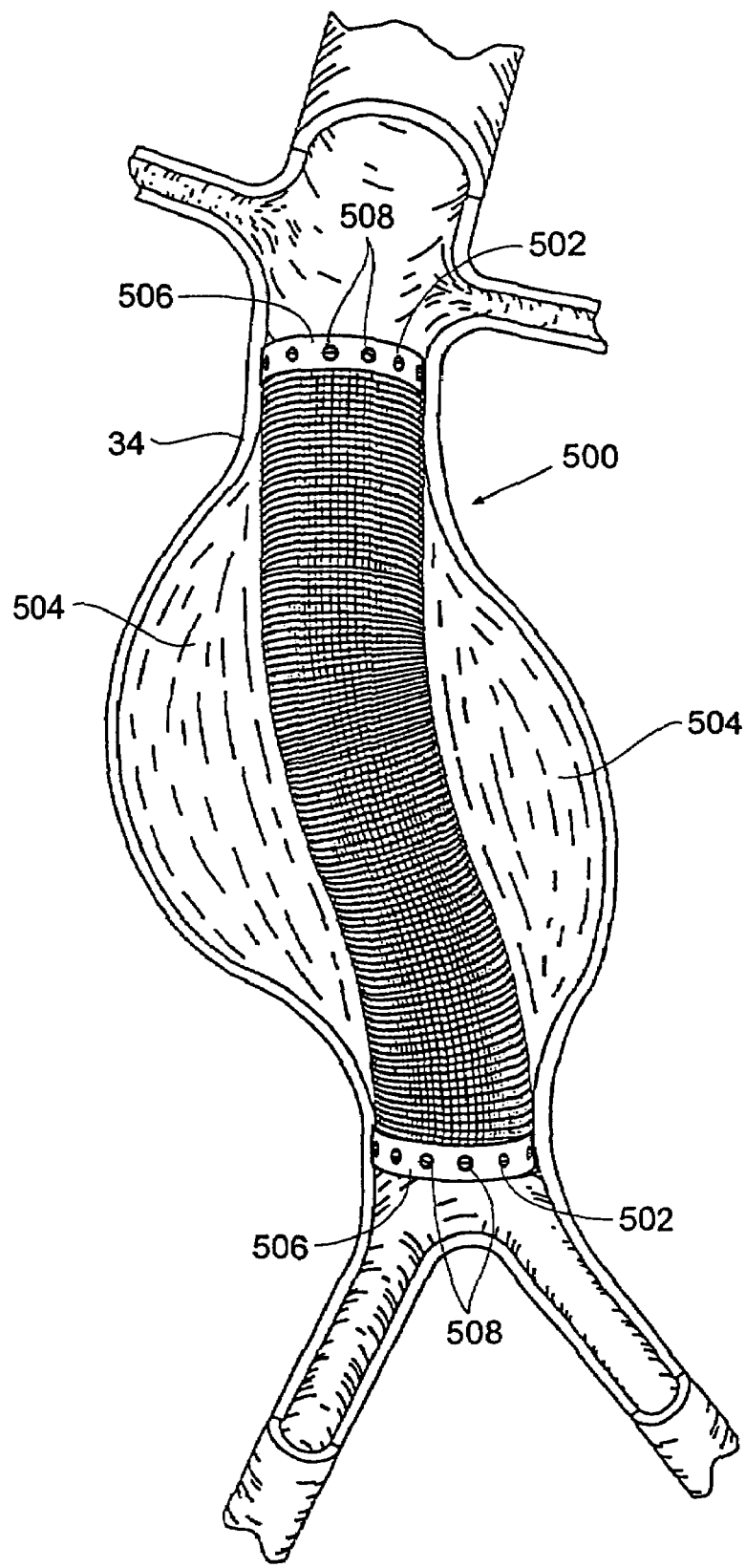
FIG. 32 is a perspective view of an endovascular prosthesis shown positioned within an abdominal aortic aneurysm, the prosthesis including an integrated fastener assembly.

FIG. 32 shows a prosthesis 500 that includes at least one integrated fastener assembly 502. FIG. 32 shows the prosthesis 500 deployed in a targeted intraluminal region, in particular, within an abdominal aortic aneurysm 504. The prosthesis 500 can be deployed elsewhere in the body.

The prosthesis 500 desirably includes a fabric material or the like carried by a support frame or scaffold 504, as previously described. The scaffold 504 can be made, e.g., from an elastic material that self-expands radially during deployment from a sheath, or from a malleable material that expands radially in response to a radially expansive force applied within the scaffold by a balloon or a mechanical expansion device.

Following deployment of the prosthesis 500 in the targeted region, the integrated fastener assembly 502 on the prosthesis 500 is manipulated to anchor the prosthesis 500 to the vessel wall. In the illustrated embodiment, the prosthesis 500 carries two integrated fastener assemblies 502, one in each end region of the prosthesis 500.

In the illustrated embodiment, each fastener assembly 502 is imbedded in a reinforced flange area 506 in the respective end region. Each fastener assembly 502 comprises an array of fasteners 508 circumferentially spaced about the flange 506. The number of fasteners 508 in the array can vary, e.g., from about two to about twelve fasteners on each flange area 506. The configuration of the array can also vary, e.g., in the circumferential array, the fasteners 508 can by axially spaced apart as well.

Figure 34:
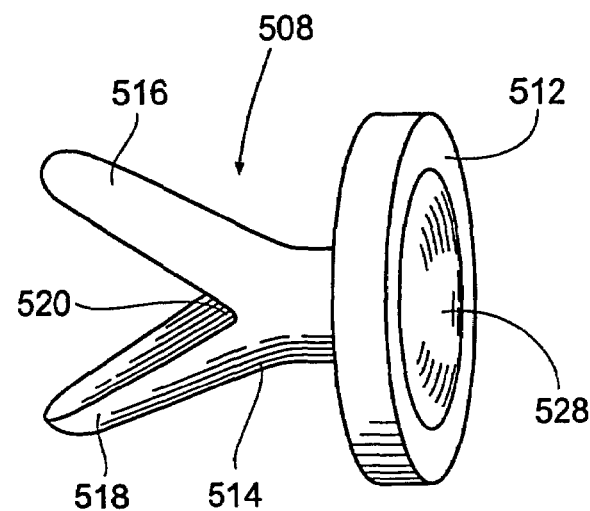
FIG. 34 is a side view of a fastener that forms a part of the integrated fastener assembly shown in FIG. 33, the fastener having a stem, which is shown in a normally spread-apart condition before its association with the integrated fastener assembly.

The fasteners 508 can be formed of a metal or plastic material and can be variously constructed. In the illustrated embodiment, each fastener 508 includes a disc-shaped head 512 and a stem 514 that is bifurcated into two wings 516 and 518, which are joined by a plastic or memory material hinge region 520. The material of the hinge region 520 is formed with a resilient memory that biases the wings 516 and 518 to a spread-apart condition (as FIG. 34 shows).

Figure 35:
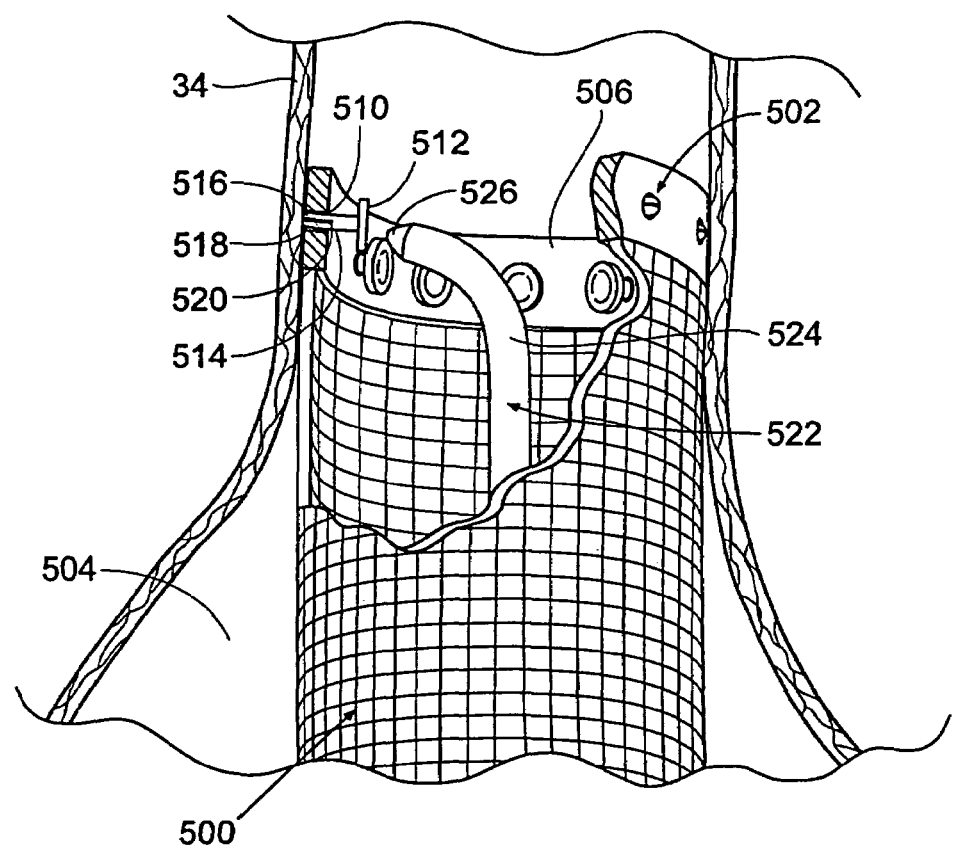
FIG. 35 is a side view of the fastener shown in FIG. 34, the fastener stem now being shown in a closed condition and housed within a grommet that forms a part of the integrated fastener assembly.

Each fastener 508 is carried within a grommet 510 on the flange area 506 (see FIG. 35). When the hinge region 520 is confined within the grommet 510 (as FIG. 35 shows), the wings 516 and 518 are retained against the resilient memory in an adjacent, closed condition. In response to the application of a pushing or punching force on the head 512 (see FIG. 35), the wings 516 and 518 are advanced in the closed condition out of the grommet 510, and into and through the adjacent vessel wall (see FIG. 36). Upon continued advancement, the hinge region 520 is freed from the confines of the grommet 510 (see FIG. 37). As a result, the wings 516 and 518 resiliently spring into their normal spread-apart condition.

Figure 33:
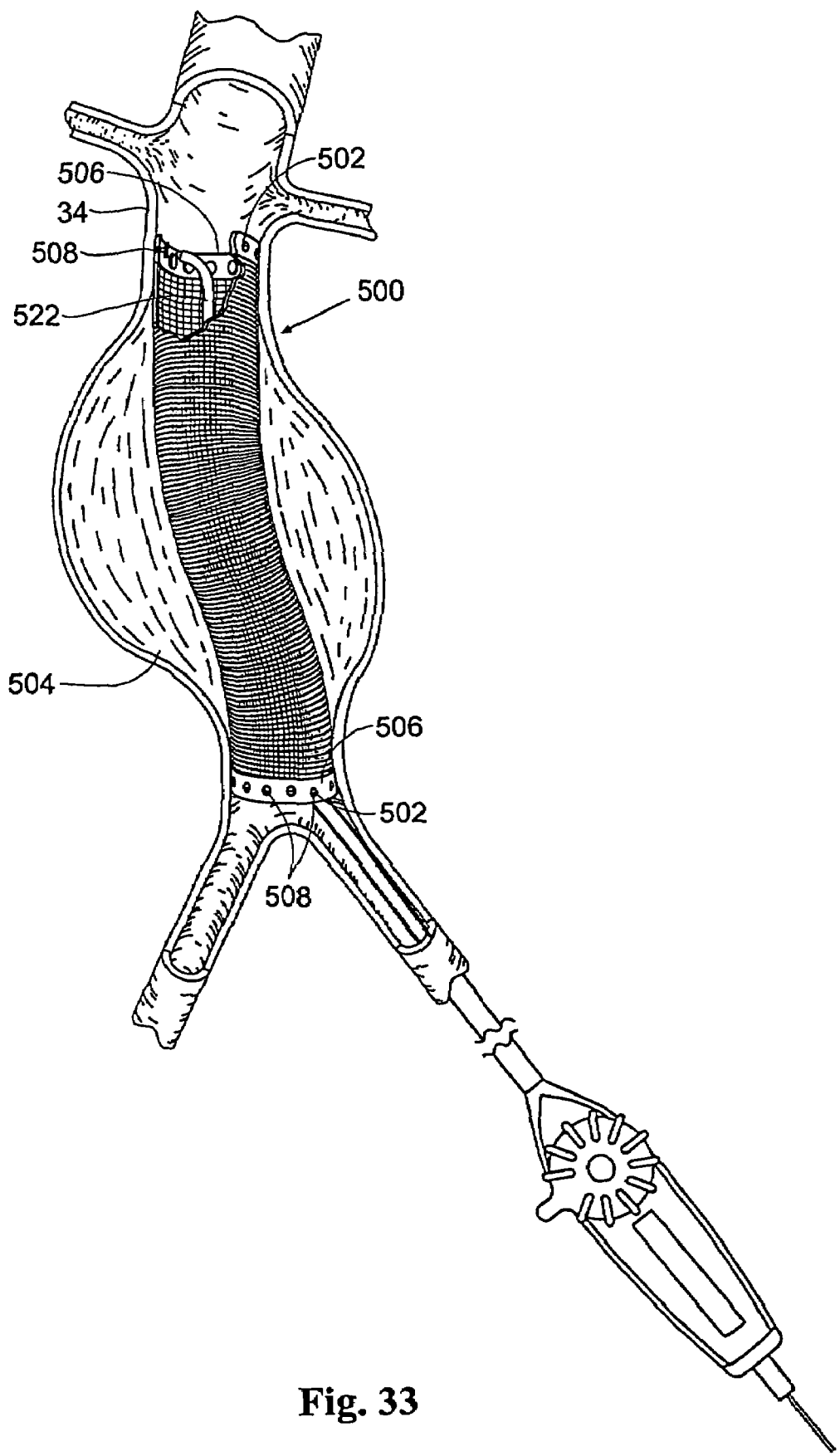
FIG. 33 is a perspective view of the endovascular prosthesis shown in FIG. 32, with an intraluminal tool deployed to operatively interact with the integrated fastener assembly, to temporarily or permanently anchor the prosthesis to the wall of the vessel.

In this arrangement, an intraluminal tool 522 (see FIG. 33) is deployed into the prosthesis 500 to exert a pushing or punching force upon the head 512 of a given fastener 508. In the illustrated embodiment, the tool 522 comprises a catheter 524 that carries a punch member 526 at its distal end. In a desired arrangement, the distal end of the catheter 524 is steerable, to aid in establishing point contact between the punch member 526 and the head 512 of the given fastener 508. The head 512 can include a recess 528 to receive and stabilize the tip of the punch member 526 with respect to the head 512 during use (see FIG. 34).

Figure 36:
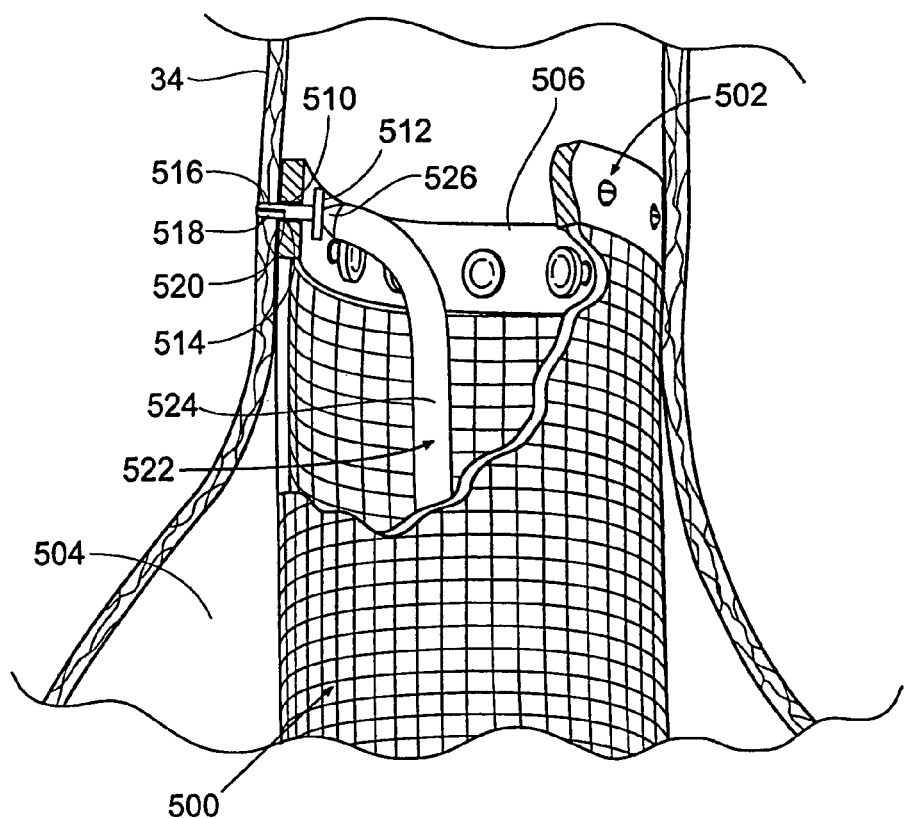
FIGS. 36 and 37 are side views showing the use of the intraluminal tool shown in FIG. 33 to apply force to drive the fastener from its position shown in FIG. 35 and through the vessel wall.
Figure 37:
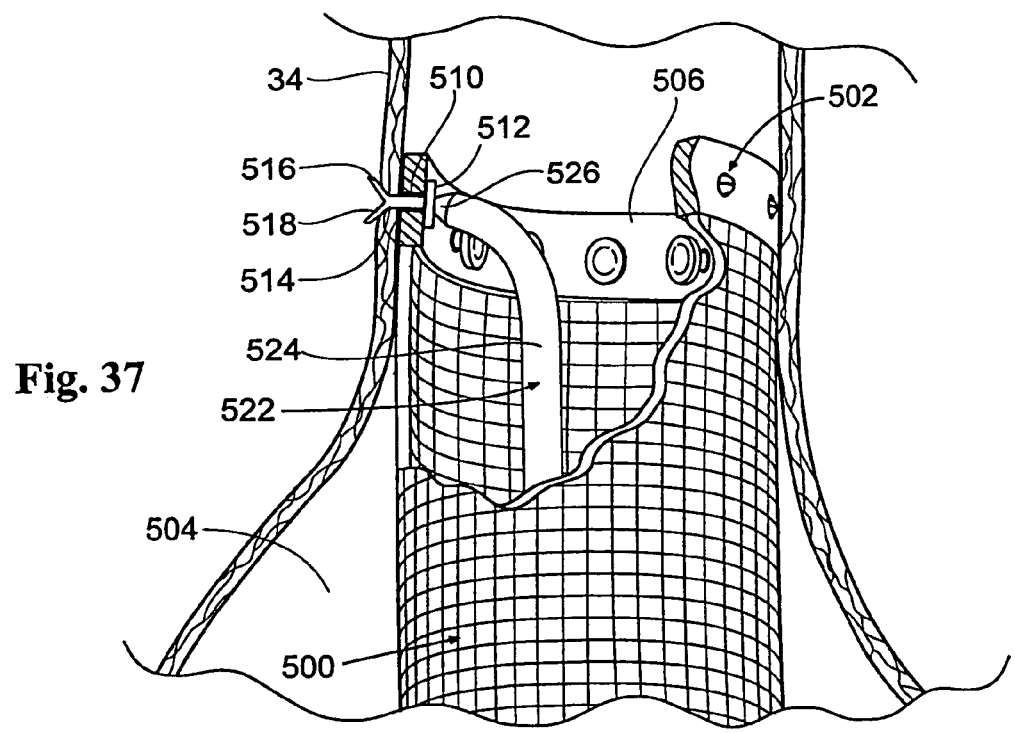
Figure 38:
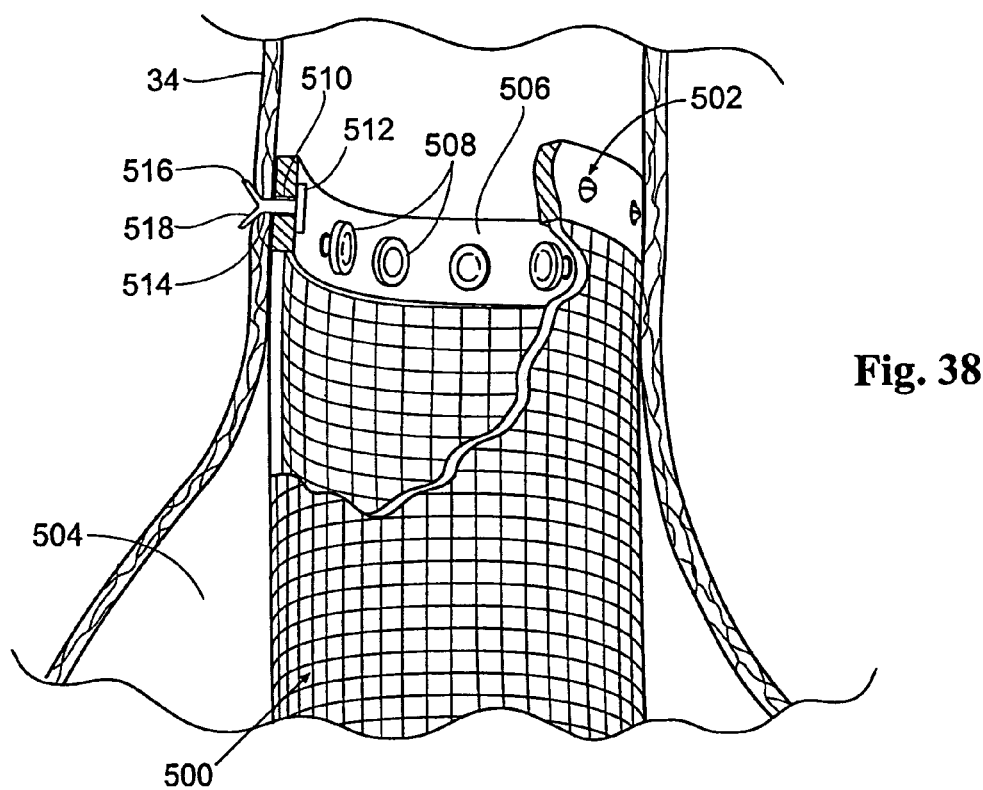
FIG. 38 is the integrated fastener assembly after deployment to anchor a prosthesis to a vessel wall.

In use, the punch member 526 is manipulated to apply a pushing or punching force upon the selected fastener head 512. As FIGS. 35 and 36 show, the application of the pushing force by the punch member 526 forces the wings 516 and 518 against the near side of the vessel wall 34. The wings 516 and 518 are still in their closed condition, because the hinge region 520 is still confined within the grommet 510. The closed wings 516 and 518 form an obturator that penetrates tissue as it advances to the far side of the vessel wall. As the hinge region 510 is freed from the grommet 510 (FIG. 37), the wings 516 and 518 resiliently return to their spread-apart condition against the far side of the vessel wall. Upon removal of the punch member 526 (see FIG. 38), the head 512 and spread-apart wings 516 and 518 remain in their mutually opposed condition in the vessel wall, to secure the prosthesis 500 against the vessel wall. In use, the physician locates and manipulates the punch member 526 in succession against each fastener 508, to complete the anchorage of the prosthesis 500 to the vessel wall.

Figure 39:
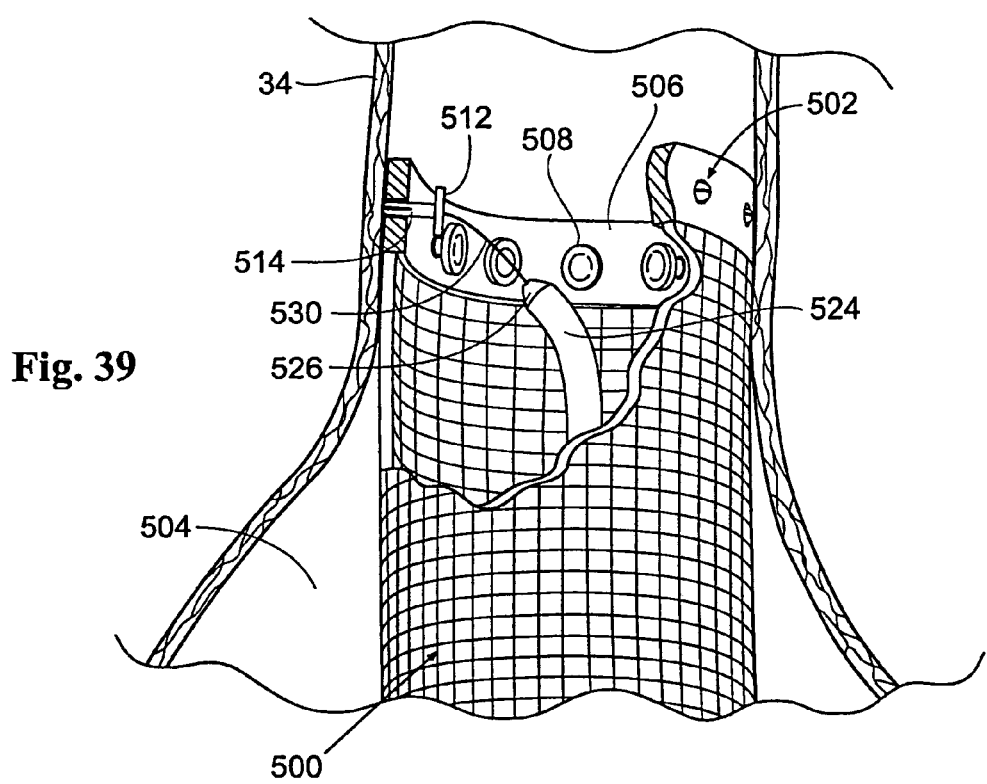
FIG. 39 is a side view showing the use of a tracking wire to guide a intraluminal tool into contact with a fastener, so that force can be applied to drive the fastener through the vessel wall.

In one embodiment (see FIG. 39), each fastener 508 can include a tracking wire 530 that is releasably coupled to the head 512. The tracking wire 530 extends from the head 512 outside the body for access outside the vessel. In this arrangement, the punch member 526 includes a lumen to accommodate passage of the tracking wire 530. The tracking wire 530 guides the punch member 526 in an intraluminal path to the respective fastener 508. After the punch member 526 is manipulated to drive the fastener 508 into the vessel wall, the punch member 526 can be withdrawn over the tracking wire 530. The tracking wire 530 can be released from the now-secured head 512, e.g., by applying a moderate pulling force upon the tracking wire 530. The tracking wire 530 can then be withdrawn. The punch member 526 is sequentially guided over another tracking wire 530 for interaction with another one of the fasteners 508, until a desired degree of anchorage is achieved.

In an alternative embodiment, an integrated fastener assembly 502 on the prosthesis 500 can be used to temporarily tack the prosthesis 500 in place while a permanent anchoring technique is carried out. For example, in this arrangement, after using the integrated fastener assembly 502 to temporarily hold the prosthesis 500 in a desired location, the separate helical fasteners 28 are deployed in the manner previously described, to permanently anchor the prosthesis 500 against the vessel wall.

It will be appreciated that the components and/or features of the preferred embodiments described herein may be used together or separately, while the depicted methods and devices may be combined or modified in whole or in part. It is contemplated that the components of the directing device, fastener applier and helical fastener may be alternately oriented relative to each other, for example, offset, bi-axial, etc. Further, it will be understood that the various embodiments may be used in additional procedures not described herein, such as vascular trauma, arterial dissections, artificial heart valve attachment and attachment of other prosthetic device within the vascular system and generally within the body.

The preferred embodiments of the invention are described above in detail for the purpose of setting forth a complete disclosure and for the sake of explanation and clarity. Those skilled in the art will envision other modifications within the scope and sprit of the present disclosure.

We claim:

1. A method for repairing a diseased or damaged section of an aorta comprising
   (i) providing a system comprising
      at least one tissue-piercing fastener having a sharpened distal tip for piercing and penetrating tissue,
      a fastener attachment assembly sized and configured to be deployed from a remote access site to a targeted endovascular region, the fastener attachment assembly including
         an intraluminal directing device defining an access path and including a deflectable distal region, and an intraluminal fastener applier separate from the intraluminal directing device and being sized and configured for advancement into the intraluminal directing device along the access path and retrieval from the intraluminal directing device along the access path, the intraluminal fastener applier including an actuated member that is selectively operable to generate an implantation force in an implantation force direction to implant the tissue-piercing fastener by causing the sharpened distal tip to pierce and penetrate the tissue in the targeted endovascular region, and means associated with the fastener attachment assembly for applying a resolving force in a direction different than the implantation force direction within the targeted endovascular region to resolve at least a portion of the implantation force, (ii) first, introducing the intraluminal directing device separately from intraluminal fastener applier from a remote access site to a location within a prosthesis that has been deployed at a target site in an aorta where the diseased or damaged section exists;

(iii) establishing the access path to a desired fastening site on the prosthesis by manipulating the intraluminal directing device within the prosthesis to orient the distal region with respect to the desired fastening site;

(iv) and then advancing the intraluminal fastener applier from the remote access site into the intraluminal directing device along the access path to the desired fastening site;

(v) anchoring the prosthesis by operating the actuated member to generate an implantation force to implant the tissue-piercing fastener into tissue at the desired fastening site while the means applies a resolving force to resolve within the targeted site within an aorta at least a portion of the implantation force, (vi) and then separating the intraluminal fastener applier from the intraluminal directing device by retrieving the intraluminal fastener applier from the intraluminal directing device along the access path back to the remote access site.

2. A method according to claim 1
wherein (iii) includes rotating the intraluminal directing device and/or deflecting the distal region.

3. A method according to claim 1
wherein the prosthesis includes at least one self-expanding scaffold, and
wherein (ii) comprises releasing the prosthesis from constraint to permit the at least one scaffold of the prosthesis to self-expand at the target site.

4. A method according to claim 1
wherein the prosthesis includes at least one malleable scaffold, and
wherein (ii) comprises applying a radially expansive force within the prosthesis to cause expansion of the at least one scaffold.

5. A method according to claim 1
wherein the intraluminal directing device includes a passage that defines the access path,
wherein (iv) includes advancing the intraluminal fastener applier from the remote access site into the intraluminal directing device through the passage to the desired fastening site, and wherein (vi) includes separating the intraluminal fastener applier from the intraluminal directing device by retrieving the intraluminal fastener applier from the intraluminal directing device through the passage back to the remote access site.

6. A method according to claim 5
wherein the passage comprises an interior lumen.

7. A method according to claim 1
further including, after (vi), (vii) loading at the remote access site another tissue-piercing fastener having a sharpened distal tip for piercing and penetrating tissue on the actuated member.

8. A method according to claim 7
further including repeating (iv), then (v), then (vi), and then (vii) until a desired number of tissue-piercing fasteners are implanted.

9. A method for repairing a diseased or damaged section of an aorta comprising
(i) providing a system comprising
at least one tissue-piercing fastener having a sharpened distal tip for piercing and penetrating tissue,
a fastener attachment assembly sized and configured to be deployed from a remote access site to a targeted endovascular region, the fastener attachment assembly including
an intraluminal directing device defining an access path and including a deflectable distal region, and
an intraluminal fastener applier separate from the intraluminal directing device and being sized and configured for advancement into the intraluminal directing device along the access path and retrieval from the intraluminal directing device along the access path, the intraluminal fastener applier including an actuated member that is selectively operable to generate an implantation force in an implantation force direction to implant the tissue-piercing fastener by causing the sharpened distal tip to pierce and penetrate the tissue in the targeted endovascular region, and
means associated with the fastener attachment assembly for applying a resolving force in a direction different than the implantation force direction within the targeted endovascular region to resolve at least a portion of the implantation force,
(ii) first, introducing the intraluminal directing device separately from intraluminal fastener applier from a remote access site to a location within a prosthesis that has been deployed at a target site in an aorta where the diseased or damaged section exists, thereby establishing an access path;
(iii) and then advancing the intraluminal fastener applier from the remote access site into the intraluminal directing device along the access path;
(iv) anchoring the prosthesis by manipulating the intraluminal directing device within the prosthesis to orient the distal region with respect to the desired fastening site and by operating the actuated member to generate an implantation force to implant the tissue-piercing fastener into tissue at the desired fastening site while the means applies a resolving force to resolve within the targeted site within an aorta at least a portion of the implantation force,
(v) and then separating the intraluminal fastener applier from the intraluminal directing device by retrieving the intraluminal fastener applier from the intraluminal directing device along the access path back to the remote access site.

10. A method according to claim 9
wherein (iv) includes rotating the intraluminal directing device and/or deflecting the distal region.

11. A method according to claim 9
wherein the prosthesis includes at least one self-expanding scaffold, and
wherein (ii) comprises releasing the prosthesis from constraint to permit the at least one scaffold of the prosthesis to self-expand at the target site.

12. A method according to claim 9
wherein the prosthesis includes at least one malleable scaffold, and
wherein (ii) comprises applying a radially expansive force within the prosthesis to cause expansion of the at least one scaffold.

13. A method according to claim 9
wherein the intraluminal directing device includes a passage that defines the access path,
wherein (iii) includes advancing the intraluminal fastener applier from the remote access site into the intraluminal directing device through the passage to the desired fastening site, and
wherein (v) includes separating the intraluminal fastener applier from the intraluminal directing device by retrieving the intraluminal fastener applier from the intraluminal directing device through the passage back to the remote access site.

14. A method according to claim 13
wherein the passage comprises an interior lumen.

15. A method according to claim 9
further including, after (v), (vi) loading at the remote access site another tissue-piercing fastener having a sharpened distal tip for piercing and penetrating tissue on the actuated member.

16. A method according to claim 15
further including repeating (iii), then (iv), then (v), and then (vi) until a desired number of tissue-piercing fasteners are implanted.

\* \* \* \* \*